(12) United States Patent
Griep-Raming

(10) Patent No.: US 10,607,822 B2
(45) Date of Patent: Mar. 31, 2020

(54) METHOD AND APPARATUS FOR ISOTOPE RATIO MASS SPECTROMETRY

(71) Applicant: Thermo Fisher Scientific (Bremen) GmbH, Bremen (DE)

(72) Inventor: Jens Griep-Raming, Ganderkesee (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/887,520

(22) Filed: Feb. 2, 2018

(65) Prior Publication Data

US 2018/0226238 A1 Aug. 9, 2018

(30) Foreign Application Priority Data

Feb. 7, 2017 (GB) .................................. 1701986.0
Nov. 9, 2017 (GB) .................................. 1718521.6

(51) Int. Cl.
*H01J 49/00* (2006.01)
*H01J 49/38* (2006.01)
(Continued)

(52) U.S. Cl.
CPC ...... *H01J 49/0031* (2013.01); *H01J 49/0036* (2013.01); *H01J 49/0459* (2013.01);
(Continued)

(58) Field of Classification Search
CPC ............... H01J 49/0027; H01J 49/0031; H01J 49/0036; H01J 49/0459; H01J 49/282;
(Continued)

(56) References Cited

U.S. PATENT DOCUMENTS

| 6,031,228 A * | 2/2000 | Abramson | .......... H01J 49/0027 250/281 |
| 2002/0072126 A1* | 6/2002 | Chervet | ................ G01N 30/32 436/161 |

(Continued)

FOREIGN PATENT DOCUMENTS

| EP | 2594936 A2 | 5/2013 |
| WO | 02/29399 A2 | 4/2002 |

(Continued)

OTHER PUBLICATIONS

"Fluid Dynamics and the Bernoulli Equation", http://physics.bu.edu/~duffy/py105/Bernoulli.html (Year: 1999).*
(Continued)

*Primary Examiner* — David E Smith
(74) *Attorney, Agent, or Firm* — David A. Schell

(57) ABSTRACT

A method of isotope ratio mass spectrometry comprising: flowing a liquid mobile phase through a separation device; reducing the flow rate of the mobile phase through the separation device for at least a portion of time that at least one molecular species is emerging from the separation device to achieve a desired isotope ratio precision, wherein the flow rate is reduced from a first rate to a second rate corresponding to a higher theoretical plate height of the separation device; and mass analyzing the molecular species that has emerged from the separation device at least while the flow rate is reduced; and determining at least one isotope ratio from the intensities of mass peaks of at least two isotopologues, wherein the mass analysis is performed with mass resolving power high enough to resolve the two most abundant mass peaks at the nominal mass of at least one of the isotopologues.

25 Claims, 19 Drawing Sheets

(51) Int. Cl.

| H01J 49/40 | (2006.01) |
|---|---|
| H01J 49/28 | (2006.01) |
| H01J 49/04 | (2006.01) |
| G01N 30/72 | (2006.01) |
| G01N 30/86 | (2006.01) |
| G01N 30/32 | (2006.01) |

(52) U.S. Cl.
CPC ............ *H01J 49/282* (2013.01); *H01J 49/38* (2013.01); *H01J 49/40* (2013.01); *G01N 30/7233* (2013.01); *G01N 30/8658* (2013.01); *G01N 2030/324* (2013.01)

(58) Field of Classification Search
CPC ...... H01J 49/38; H01J 49/40; G01N 30/7233; G01N 30/8658; G01N 2030/324
See application file for complete search history.

(56) References Cited

U.S. PATENT DOCUMENTS

| 2003/0226394 | A1* | 12/2003 | Hilkert | B01D 59/44 |
| | | | | 73/23.39 |
| 2008/0081782 | A1* | 4/2008 | Li | C07K 1/13 |
| | | | | 530/352 |
| 2008/0092639 | A1* | 4/2008 | Lee | G01N 30/32 |
| | | | | 73/61.52 |
| 2008/0265152 | A1* | 10/2008 | Bateman | B01D 59/44 |
| | | | | 250/283 |
| 2009/0305322 | A1* | 12/2009 | Hegg | C12Q 1/02 |
| | | | | 435/29 |
| 2011/0212536 | A1* | 9/2011 | Krummen | G01N 30/462 |
| | | | | 436/161 |
| 2013/0103337 | A1* | 4/2013 | Eiler | G16C 20/20 |
| | | | | 702/86 |
| 2014/0097338 | A1 | 4/2014 | Eiler | |
| 2015/0041635 | A1* | 2/2015 | Green | H01J 49/0036 |
| | | | | 250/282 |
| 2015/0340216 | A1* | 11/2015 | Kwiecien | G06K 9/00543 |
| | | | | 250/282 |

FOREIGN PATENT DOCUMENTS

| WO | 02/077016 A2 | 10/2002 |
| WO | 2010/030178 A1 | 3/2010 |
| WO | 2016/112386 A1 | 7/2016 |

OTHER PUBLICATIONS

Eiler et al, "The Q-Exactive GC Orbitrap as a Gateway to High-Dimensionality Studies of Molecular Isotropic Structure", presentation at Clumped Isotope Workshop (2016), p. 1-35 (Year: 2016).*

O'Connor et al., "Internal Calibration on Adjacent Samples (InCAS) with Fourier Transform Mass Spectrometry", Anal. Chem. 2000, 72, pp. 5881-5885.

Breidbach, "Improved precision of measured isotope ratio through peak parking and scan-based statistics in IDMS of small organic molecules". Poster ThOS36-02, 20th International Mass Spectrometry Conference 2014, Geneva, CH, p. 1-2.

Eiler et al., "The 100 isotopologue challenge: Orbitrap mass spectrometry as a means of high-dimension clumped and position-specific isotope analysis", Poster, ASMS 2016.

Eiler et al., "The Orbitrap as a gateway to high-dimensionality studies of molecular isotopic structure", Abstract, 5th International Clumped Isotope Workshop, St. Petersburg, FL (2016).

Eiler et al., "The Q-Exactive GC Orbitrap as a gateway to high-dimensionality studies of molecular isotopic structure", presentation at Clumped Isotope Workshop (2016), p. 1-35.

Sessions et al., "Moving-Wire Device for Carbon Isotopic Analyses of Nanogram Quantities of Nonvolatile Organic Carbon", Anal. Chem. 2005, 77, pp. 6519-6527.

Teffera et al., "Continuous-Flow Isotope Ratio Mass Spectrometry Using the Chemical Reaction Interface with Either Gas or Liquid Chromatographic Introduction", Anal. Chem. 1996, 68, pp. 1888-1894.

* cited by examiner

| No | Time | Flow [ml/min] | %B | Curve |
|---|---|---|---|---|
| 1 | 0.000 | | Equilibration | |
| 2 | 0.000 | 0.200 | 0.0 | 5 |
| 3 | New Row | | | |
| 4 | 0.000 | 0.200 | Run | |
| 5 | 0.500 | 0.200 | 0.0 | 5 |
| 6 | 0.500 | 0.200 | 50.0 | 5 |
| 7 | 3.000 | 0.200 | 50.0 | 5 |
| 8 | 3.000 | 0.200 | 80.0 | 5 |
| 9 | 3.300 | 0.200 | 80.0 | 5 |
| 10 | 3.300 | 0.200 | 0.0 | 5 |
| 11 | New Row | | | |
| 12 | 5.000 | | Stop Run | |

FIG. 8 (Cont'd)

| No | Time | Flow [ml/min] | %B | Curve |
|----|------|---------------|------|-------|
| 1 | 0.000 | | Equilibration | |
| 2 | 0.000 | 0.200 | 0.0 | 5 |
| 3 | New Row | | | |
| 4 | 0.000 | 0.200 | Run | |
| 5 | 0.500 | 0.200 | 0.0 | 5 |
| 6 | 0.500 | 0.200 | 50.0 | 5 |
| 7 | 8.500 | 0.200 | 50.0 | 5 |
| 8 | 8.500 | 0.200 | 80.0 | 5 |
| 9 | 9.000 | 0.200 | 80.0 | 5 |
| 10 | 9.000 | 0.200 | 0.0 | 5 |
| 11 | New Row | | | |
| 12 | 11.000 | | Stop Run | |

*FIG. 11 (Cont'd)*

METHOD AND APPARATUS FOR ISOTOPE RATIO MASS SPECTROMETRY

FIELD

The invention relates to the field of mass spectrometry. The invention especially relates to isotope ratio mass spectrometry (IRMS), and more particularly IRMS coupled to liquid chromatography. The invention provides both methods and apparatus.

BACKGROUND

Conventionally, accurate and precise isotope measurements are made on magnetic sector mass spectrometers, in particular magnetic sector mass spectrometers utilizing a multi-collector for simultaneous detection of isotopes. Prior to analysis, a sample typically undergoes oxidation, pyrolysis and/or reduction at an elevated temperature to produce gaseous molecules, for example one or more of $CO_x$, $NO_x$, $N_2$, $H_2O$ and $SO_2$ (x=1 or 2). The gases are then introduced into the isotope ratio mass spectrometer for isotopic analysis. In the isotope ratio spectrometer, the gases are ionized and the ratios of corresponding isotopes are measured for example by comparing outputs of different collectors. The ratios of the isotopes of interest are typically measured relative to an isotopic standard in order to eliminate any bias or systematic error in the measurements.

Recently, it has been shown that electrostatic orbital trap mass spectrometers, such as an ORBITRAP mass spectrometer (Thermo Scientific), are also capable of measuring precise isotope ratios that should, in principle, be accurate as well (John Eiler, presentation at Clumped Isotope Workshop, January 2016; John Eiler et al. Poster at ASMS 2016 conference). Such results have been made using an ORBITRAP mass spectrometer employing electron impact ionization coupled to a gas chromatography (GC) column and employing a peak broadener downstream of the GC column. However, the concept of a peak broadener in the form of an in-line sweep volume is difficult to implement in an LC setup because of slower diffusion in a liquid. This would cause inhomogeneities in the effluent and therefore cause the measurement to become less reproducible.

The measurement of precise and accurate isotope ratios using liquid chromatography (LC) coupled to a mass spectrometer has presented particular problems. LC is an established technique in the field of biochemistry, life science and pharmacology for the separation of molecular components in a mixture. A typical sample includes organic molecules dissolved in an organic solvent, or an aqueous solution, or a medium comprising water and an organic solvent. For such samples, separation of the molecules from the solvent is generally carried out with an organic mobile phase using techniques such as high performance liquid chromatography (HPLC), capillary-zone electrophoresis (CZE) and size-exclusion chromatography (SEC). However, coupling an isotope ratio mass spectrometer to a liquid chromatography system presents technical challenges because the LC mobile phase is often based on organic solvent, and/or includes carbon containing buffers, and therefore produces the same species of oxidation or reduction products as organic sample molecules of interest, thus interfering with the isotopic analysis. There have been various attempts at coupling liquid chromatography to IRMS, as identified below.

"Moving-wire device for Carbon Isotopic Analyses of Nanogram Quantities of Nonvolatile Organic Carbon" (A. L. Sessions, S. P. Sylva and J. M. Hayes, Anal. Chem., 2005, 77, 6519-6527) describes a method for analyzing $^{13}C$ ratios of involatile organic samples dissolved in solution. The output solution of the separation system is dried onto a nickel wire to remove the mobile phase from the sample. The residual sample is then combusted and the evolved $CO_2$ is analyzed by IRMS. However, both the precision and sensitivity of this method are limited by a high background level of $CO_2$ derived from carbon within the wire. The moving wire coupling has been unsuccessful commercially because of its inherent unreliability.

Another method of coupling a liquid chromatography system to an IRMS is presented in ""Continuous-Flow Isotope Ratio Mass Spectrometry Using the Chemical Reaction Interface with Either Gas or Liquid Chromatography Introduction" (Y. Teffera, J. Kusmierz, F. Abramson, Anal. Chem., 1996, 68, 1888-1894)". In this method, the solution exiting from the liquid chromatography system undergoes desolvation at semi-permeable membranes prior to chemical oxidation of the dry aerosol. The oxidized products are then analyzed by IRMS. However, the method described does not remove the mobile phase to the required ultra-low levels of solvent, for example, to a solvent/sample ratio better than 1:100.

Wet chemical oxidation (as used by LC-Isolink™ from Thermo Fisher Scientific) allows coupling to liquid chromatography. The solution output from the chromatography system is mixed with an oxidizing agent and supplied to an oxidation reactor. In the oxidation reactor the organic compounds are converted into $CO_2$, which is then analyzed in the IRMS. However, there is no separation of the mobile phase from the sample and, therefore, this method is not suitable for LC separation methods that utilize an organic mobile phase or liquid phase modifiers or buffers containing carbon.

In addition, problems associated with ion source fluctuations that are inherent with conventional LC-MS ion sources, such as electrospray ionization (ESI) or atmospheric pressure chemical ionization (APCI) sources, further deter the use of LC-MS for accurate and precise isotope ratio measurements.

In a recent presentation (A. Breidbach, Improved precision of measured isotope ratio through peak parking and scan-based statistics in IDMS of small organic molecules, Poster ThOS36-02, 20$^{th}$ International Mass Spectrometry Conference 2014, Geneva, CH), a method of peak parking has been used that involves cutting an LC peak out of a chromatogram and capturing the eluting species in a sample loop. The loop is then flushed and transferred to the mass spectrometer by a lower flow generated by a second pump. However, the steps of removing the sample from the main flow into a loop and then flushing to the mass spectrometer have not achieved the level of precision and accuracy that is often desired for isotope ratio measurements. Moreover, the system is complex, requiring the additional sample loop and second pump system.

Accordingly, there remains a need for precise and accurate isotope ratio determination using mass spectrometric detection coupled to LC.

SUMMARY

According to one aspect of the invention there is provided a method of isotope ratio mass spectrometry comprising:
  flowing a liquid mobile phase that contains a sample through a separation device, the sample comprising at least one molecular species having an isotope ratio to be determined;

setting or reducing the flow rate of the liquid mobile phase flowing through the separation device for at least a portion of time that the at least one molecular species is emerging from the separation device to achieve a desired isotope ratio precision;

mass analyzing the at least one molecular species that has emerged from the separation device at least while the flow rate is set or reduced; and determining from the mass analysis at least one isotope ratio of the at least one molecular species.

According to another aspect of the invention, there is provided a method of isotope ratio mass spectrometry according to claim 1.

The at least one isotope ratio can be determined from the intensities of mass peaks of at least two isotopologues of the at least one molecular species having different or the same nominal mass, preferably wherein the mass analysis is performed with mass resolving power high enough to resolve the two most abundant mass peaks at the nominal mass of at least one of the isotopologues used to determine the isotope ratio, preferably at the nominal masses of each of the isotopologues used to determine the isotope ratio. In this context, resolved shall mean that two adjacent peaks have peak tops that are distinguishable from one another, i.e. that there is a valley between them.

The at least one isotope ratio can be determined from the intensities of mass peaks of at least two isotopologues of the at least one molecular species having different or the same nominal mass, preferably wherein each isotopologue mass peak used for the isotope ratio determination is resolved from at least any other mass peaks at the same nominal mass which are more than 20% (preferably more than 10%, or more than 5%) of the intensity of the isotopologue mass peak.

The step of mass analyzing the at least one molecular species that has emerged from the separation device is performed at least while the flow rate is reduced or set to the flow rate to achieve a desired isotope ratio precision.

According to still another aspect of the invention there is provided an apparatus for isotope ratio mass spectrometry comprising:

a separation device for separating components of a sample in a liquid mobile phase, the components of the sample comprising at least one molecular species having an isotope ratio to be determined;

a mass spectrometer coupled to the separation device downstream for mass analyzing the at least one molecular species as the at least one molecular species elutes from the separation device and determining from the mass analysis at least one isotope ratio of the at least one molecular species; and a controller configured to set or reduce the flow rate of the liquid mobile phase through the separation device for at least a portion of time that the at least one molecular species is eluting from the separation device, to achieve a desired isotope ratio precision.

According to yet another aspect of the invention there is provided an apparatus for isotope ratio mass spectrometry according to claim 25.

Preferably, mass spectrometer can perform mass analysis with mass resolving power high enough to resolve the two most abundant mass peaks at the nominal mass of at least one of the isotopologues. Preferably, mass spectrometer can perform mass analysis with resolving power high enough that each isotopologue mass peak used for the isotope ratio determination is resolved from at least any other mass peaks at the same nominal mass which are more than 20% (preferably more than 10%, or more than 5%) of the intensity of the isotopologue mass peak.

The flow rate of the liquid mobile phase flowing through the separation device for at least a portion of time that the at least one molecular species is emerging from the separation device is set or reduced to achieve a desired isotope ratio precision as described hereinafter.

According to still another aspect of the invention there is provided a method of isotope ratio mass spectrometry comprising:

flowing a liquid mobile phase that contains a sample through a separation device, the sample comprising at least one molecular species having an isotope ratio to be determined;

setting the flow rate of the liquid mobile phase flowing through the separation device for at least a portion of time that the at least one molecular species is emerging from the separation device to a flow rate that enables a desired isotope ratio precision to be achieved;

mass analyzing the at least one molecular species that has emerged from the separation device at least while the flow rate is reduced;

determining from the mass analysis at least one isotope ratio of the at least one molecular species.

A separation device and a mass spectrometer are preferably provided as described above. In addition, a controller is preferably configured to set the flow rate of the liquid mobile phase through the separation device for at least a portion of time that the at least one molecular species is eluting from the separation device to a flow rate that enables a desired isotope ratio precision to be achieved. Preferably, the desired isotope ratio precision is <20‰ and more preferably, the desired isotope ratio precision is <10 δ‰. In certain embodiments, a step of reducing the flow rate is not used but rather the entire separation of the sample up to an including the elution of the at least one molecular species having an isotope ratio to be determined can be performed at a low enough flow rate that enables the desired isotope ratio precision to be achieved. Such embodiments, however, have the disadvantage that the overall analysis time is increased. Therefore, it is preferable to employ a step of reducing the flow rate for a limited time, especially for at least a portion of the time that the at least one molecular species having an isotope ratio to be determined elutes from the separation device.

The invention enables precise and accurate isotope ratio determination using mass spectrometric detection coupled to a liquid-based sample separation technique, such as LC, especially when organic solvents are utilized. The invention can also allow the use of ionization techniques that are typically amenable with LC-MS, such as atmospheric pressure ionization (API), for example electrospray ionization (ESI) and atmospheric pressure chemical ionization (APCI).

The separation device is a sample separation device for separating molecular species of a sample in a liquid phase. The separation device preferably comprises a liquid chromatography (LC) column, for example a column for high performance liquid chromatography (HPLC) or ultra-high performance liquid chromatography (UHPLC), or size-exclusion chromatography (SEC) or ion chromatography (IC). The LC column internal diameter is preferably in the range from 0.1 to 10 millimeters (mm) but smaller or larger column diameters may be employed. The type of chromatography can be, for example reversed-phase chromatography (RPC) or normal-phase chromatography (NPC). The separation device can comprise a plate for thin-layer chromatography (TLC). Preferably, the chromatography is one wherein the mobile phase at least partly comprises, or fully comprises, organic solvent. The separation device can comprise a capillary electrophoresis (CE) system, for example for capillary zone electrophoresis (CZE), or other electrophoretic techniques including capillary gel electrophoresis (CGE).

The liquid mobile phase may be an aqueous phase, or organic solvent or mixture of water and organic solvent. Preferably the liquid mobile phase comprises an amount of organic solvent (such as at least 10%, 20%, 30%, 40%, or 50% organic solvent by volume). The liquid mobile phase can comprise at least 60, 70%, 80%, 905 or 100% organic solvent by volume). The organic solvent may be a single organic solvent tor a mixture of two or more organic solvents. The liquid mobile phase composition can change according to a predetermined gradient over time. Where a gradient liquid mobile phase is used, at least a part of the gradient comprises organic solvent. The liquid mobile phase will generally be flowed through the separation device by means of at least one pump.

The sample may be, for example, one of extracts from blood, urine, saliva, cerebrospinal fluid, or other biological material, extracts from food, feedstuff, soil, dust, industrial products, incineration products, or similar, lysed cells.

The sample to be analyzed can comprises a single molecular species, or more typically comprises a plurality of molecular species, wherein there is at least one molecular species having an isotope ratio to be determined. The molecular species can be separated according to their different retention times in the separation device. The sample can be delivered into the mobile phase from an autosampler via an injection port or loop.

The at least one molecular species having an isotope ratio to be determined is or are typically an organic molecule. The molecular weight of the at least one molecular species is preferably less than 1000 Da, more preferably less than 800 Da, still more preferably less than 600 Da, and even more preferably less than 300 Da. The molecular weight of the at least one molecular species is preferably more than 45 Da, more preferably more than 60 Da.

The liquid mobile phase that contains the sample is flowed through the separation device, so that the sample comprising the at least one molecular species emerges from the separation device, preferably after being separated from at least one other molecular species, more preferably after at least a plurality of molecular species have been separated by the separation device (i.e. a plurality of molecular species of the sample emerge at different retention times from the separation device), and can be subsequently detected, i.e. mass analyzed by a downstream mass spectrometer. The at least one molecular species having an isotope ratio to be determined is preferably separated from other molecular species by the separation device. In preferred embodiments, therefore, the sample in the mobile phase is flowed through a separation device, such as a liquid chromatography column, to separate two or more molecular species of the sample. More preferably, the at least one molecular species having an isotope ratio to be determined is separated in this way from other molecular species, i.e. separated by retention time. However, it is not essential that the at least one molecular species having an isotope ratio to be determined is separated in this way from all other molecular species in the sample. It is, however, preferable that the separation is such that in the mass spectrum the presence of interference peaks from other molecular species near the mass peaks of the at least one molecular species having an isotope ratio to be determined (i.e. in a vicinity closer than 2 m/z units to the isotope peaks) is minimized. Most preferably, there are no interference peaks from other molecular species in the vicinity closer than 2 m/z units to the isotope peaks of the at least one molecular species having an isotope ratio to be determined. More preferably the mass peaks originating from the at least one molecular species having an isotope ratio to be determined (i.e. the compound of interest) are baseline separated from any other peaks of substantially co-eluting molecular species. Co-eluting species in the present context means that peaks from each species are detected in the same mass spectrum.

The mass analysis performed downstream in the mass spectrometer preferably can measure the mass-to-charge ratio (m/z) of and thereby distinguish between two or more molecular species that co-elute from the separation device (i.e. with the same or similar, i.e. overlapping, retention times), especially wherein the molecular species that co-elute have different m/z.

The liquid mobile phase is preferably flowed through the separation device initially at a first flow rate before reducing the flow rate below the first flow rate. When the flow rate is reduced it is preferably reduced to a second flow rate, below the first rate, for at least a portion of time that the at least one molecular species is emerging, i.e. eluting, from the separation device, i.e. for at least a portion of time that the at least one molecular species is in the eluate emerging from the separation device. The flow rate is preferably reduced for the whole, or at least substantially the whole, of the time that the at least one molecular species is emerging from the separation device. The flow rate can be reduced from a time before, e.g. just before, the at least one molecular species starts emerging from the separation device until at least a time when most of the at least one molecular species has emerged from the separation device, such as until a time when the at least one molecular species has substantially finished emerging from the separation device. The flow rate can remain reduced until a time after all of the at least one molecular species has emerged from the separation device. After the flow has been reduced in this way, the flow rate can be increased, typically to the first flow rate before the flow rate was reduced. This subsequent increase of the flow rate preferably occurs at a time after the at least one molecular species has substantially finished eluting from the separation device. Thus, the flow rate can be increased again to its original, higher (first) flow rate, i.e. once the at least one molecular species has substantially finished eluting from the separation device. The flow is typically increased again once the elution peak of the at least one molecular species is substantially over. The flow rate is typically reduced by a factor of at least 3, or better still at least 5 or better still at least 10, or at least 100 in some instances. The reduction factor typically has a dependence on the column size (diameter). Specific flow rates can therefore depend on the dimensions of the separation device (e.g. column internal diameter (I.D.). For the case of a liquid chromatography column and an ESI ion source, examples of typical ranges of flow rates before flow rate reduction are: 4 mm (I.D.) column=800-2000 µl/min; 2.1 mm column=150-400 µl/min; 1 mm column=30-80 µl/min; and 0.5 mm column=10-30 µl/min. It is desirable to reduce the flow rate such that the lowest stable flow rate of a typical ESI ion source is used, which is typically in the 2-5 µl/min range. The flow rate is thus typically reduced by a factor of: 160-1000 for a 4 mm column; 30-200 for a 2.1 mm column; 5-40 for a 1 mm column; and 2-15 for a 0.5 mm column. Herein the cross section of the chromatography column is assumed to be circular.

Preferably, the separation device is a liquid chromatography (LC) column (for example either an HPLC or UHPLC column). The LC column has an internal diameter and preferably the step of reducing the flow rate comprises reducing the flow rate to a value in mL/min that is less than half the value given by 0.06×(internal diameter in mm)$^2$. This formula has been found empirically to define a suitable reduced flow rate. In some embodiments employing an LC column as separation device, the flow rate of the liquid mobile phase through the separation device is set for at least a portion of time that the at least one molecular species is eluting from the separation device, optionally the whole time of the separation, to a flow rate that enables a desired isotope ratio precision to be achieved. This set flow rate is preferably given by a value in mL/min that is less than half the value given by 0.06×(internal diameter in mm)$^2$. A set or reduced flow rate that is suitable has also been found generally to be lower than about 0.5× the lower limit of the column manufacturer's recommended flow rate range for optimum chromatographic resolution. It is known that an optimum flow rate in chromatography can be determined from the Van Deemter equation, which defines a dependence of the optimum flow rate on the linear flow velocity of the mobile phase. The optimum flow rate also scales with the square of the column diameter (for circular cross section columns). The set or reduced flow rate can be lower than about 0.5× the optimum flow rate (i.e. flow rate for minimal height equivalent to a theoretical plate (HETP)), i.e. as given by the Van Deemter equation.

$$HETP = A + B/u + C \cdot u$$

Where

HETP=height equivalent to a theoretical plate, a measure of the resolving power of the column [m]

A=Eddy-diffusion parameter [m]

B=Diffusion coefficient of the eluting particles in the longitudinal direction [m$^2$ s$^{-1}$]

C=Resistance to mass transfer coefficient of the analyte between mobile and stationary phase [s]

u=Linear Velocity [m s$^{-1}$]

A schematic Van Deemter plot of the general relationship between the HETP and the flow rate for an HPLC column is shown in FIG. 15. The optimum flow rate for the column occurs at the minimum height of a theoretical plate as shown. Preferably, the first flow rate in the invention is at or close to the optimum (i.e. the optimum flow rate corresponding to the minimum theoretical plate height of the separation device or column). The first flow rate should desirably be at least 50% of the optimum flow rate, or, with increasing preference, at least 70%, or at least 80%, or at least 90% of the optimum flow rate. In some embodiments, the first flow rate can be in the range +/−50% of the optimum flow rate as indicated in FIG. 15, more preferably +/−30%, or +/−20%, or most preferably +/−10% of the optimum flow rate. The second flow rate is lower than the first flow rate but corresponds to a higher theoretical plate height. The higher theoretical plate height corresponds to a lower chromatographic separation efficiency. However, it is has been found that such a reduced flow rate gives rise to an improvement in the precision of isotope ratio measurements by high resolution accurate mass spectrometry as the molecular species emerge from the separation device. Desirably, the second flow rate is less than 50% of the optimum flow rate and, with increasing preference, can be less than 40%, or less than 30%, or less than 20%, or less than 10% of the optimum flow rate. Some examples of preferred embodiments can utilize the following first and second flow rates:

(i) a first flow rate that is at least 50% of the optimum flow rate and a second flow rate that is less than 50% of the optimum flow rate, preferably wherein the second flow rate is reduced relative to the first rate by a factor of at least 2;

(ii) a first flow rate that is at least 70% of the optimum flow rate and a second flow rate that is less than 30% of the optimum flow rate, preferably wherein the second flow rate is reduced relative to the first rate by a factor of at least 3;

(iii) a first flow rate that is at least 80% of the optimum flow rate and a second flow rate that is less than 20% of the optimum flow rate, preferably wherein the second flow rate is reduced relative to the first rate by a factor of at least 5;

(iv) a first flow rate that is at least 90% of the optimum flow rate and a second flow rate that is less than 10% of the optimum flow rate, preferably wherein the second flow rate is reduced relative to the first rate by a factor of at least 10;

(v) a first flow rate that is +/−50% of the optimum flow rate and a second flow rate that is less than 50% of the optimum flow rate, preferably wherein the second flow rate is reduced relative to the first rate by a factor of at least 2;

(vi) a first flow rate that is +/−30% of the optimum flow rate and a second flow rate that is less than 30% of the optimum flow rate, preferably wherein the second flow rate is reduced relative to the first rate by a factor of at least 3;

(vii) a first flow rate that is +/−20% of the optimum flow rate and a second flow rate that is less than 20% of the optimum flow rate, preferably wherein the second flow rate is reduced relative to the first rate by a factor of at least 5;

(viii) a first flow rate that is +/−10% of the optimum flow rate and a second flow rate that is less than 10% of the optimum flow rate, preferably wherein the second flow rate is reduced relative to the first rate by a factor of at least 10.

Preferably, the above examples of first and second flow rates are also subject to the criteria that the second flow rate is reduced relative to the first rate by a factor of at least 2, or at least 3, or better still at least 5, or even better still at least 10, or at least 20, or at least 50, or at least 100.

The reduction of the flow rate can be achieved in different ways. In one preferred embodiment, the speed of the pump (i.e. the pressure of the pumping) that drives the flow of mobile phase through the separation device can be reduced. The pump is located upstream of the separation device. In another preferred embodiment, the flow can be split upstream of the separation device so that a reduced flow rate of mobile phase passes through the separation device, e.g. so that a portion of the mobile phase flow is diverted into a branch flow path upstream of the separation device and a portion is passed through the separation device. An activated valve can be activated to divert the flow through the branch line when the reduced flow rate through the separation device is required. The speed of the pump can be maintained in this embodiment, or it can be changed along with diversion of the flow. The diversion of flow can be provided by means of a T junction or other multi-way junction (3-way or more) positioned in the flow path of the mobile phase upstream of the separation device and at least one valve situated on a branch flow path leading from the junction for controlling flow into the branch flow path. The diverted flow may lead to waste or be re-circulated or recycled. The flow rate need not be stepped between only two discrete flow rates but can be changed according to a programmed gradient of flow rates. For example, the flow rate can be gradually reduced and then gradually increased, or can go through two or more different gradients of flow reduction and/or subsequently two or more gradients of flow increase again. The controller configured to reduce the flow rate of the liquid mobile phase through the separation device can be a controller that controls the separation system comprising the separation device (such as an LC system) and mass spectrometer. The controller preferably comprises a computer system that receives input data, for example from measured mass spectra, of the retention time for the peak of interest (i.e. for the molecular species having an isotope ratio to be determined) and from the input data controls the separation system to reduce the flow rate in accordance with the invention. The controller, for example, can control the pump speed of a pump of the separation system (e.g. LC system) and/or control the activation of one or more valves to control flow through the separation system. The controller may be configured to control the flow of the liquid mobile phase through the separation device, i.e. to flow the liquid mobile phase through the separation device for a first portion of time at a first flow rate and to reduce the flow rate of the liquid mobile phase through the separation device from the first flow rate to a second flow rate lower than the first flow rate for at least a portion of time that the at least one molecular species is eluting from the separation device The mass analyzing of the at least one molecular species that has emerged from the separation device preferably takes place as the molecular species is emerging from the separation device by flowing the eluate from the separation device into the mass spectrometer. Alternatively, the at least one molecular species having an isotope ratio to be determined eluting from the sample separation device can be collected and stored for mass analysis offline. For example, the eluate could be collected in well plates and later introduced by infusion or nanospray into a mass spectrometer for mass analysis.

Mass analyzing the at least one molecular species having an isotope ratio to be determined that has emerged from the separation device is preferably performed over at least the time when the flow rate of the liquid mobile phase is reduced. The reduction in flow rate has the effect that the peak width (or elution time, i.e. the time it spends in the eluate) is increased for the at least one molecular species having an isotope ratio to be determined. Thus, the total mass analysis time for the at least one molecular species having an isotope ratio to be determined can be effectively extended by the reduction in flow rate, e.g. by increasing the number of measurement points by a factor of the ratio of the peak widths (e.g. peak width with flow reduction/peak width without flow reduction). Preferably, the signal intensity is not significantly affected by the reduction in flow rate. This is the case for many of the preferred ionization methods employed in the mass spectrometer when coupling to a liquid separation like LC, such as an electrospray ionization method. Thus, overall the flow reduction provides better precision of the mass analysis measurement and thereby improved precision of the isotope ratio determination. The isotope ratio precision generally scales with the inverse of the square root of the number of mass spectra recorded (approximately the measurement time) such that longer measurement times provide more precise results. The reduction in flow rate is maintained for at least as long as it takes to achieve the desired precision. Generally, it is not of further benefit to keep the flow rate reduced for longer than required to achieve this precision as it could lead to unnecessarily long analysis times. Preferably, the desired isotope ratio precision is <20 δ‰, preferably (in order of increasing preference) <15 δ‰, or <10 δ‰, or <7 δ‰, or <5 δ‰, or <3 δ‰, or <1 δ‰, or <0.5 δ‰, or <0.1 δ%. In this way, a determination of the duration of the analysis can be based on the expected precision. As an example, if it is desired to achieve 1‰ precision, it could be experimentally determined for example that the precision achieved with 10 scans is 17‰ (one scan can result in one spectra). Therefore, it can be calculated that at least $10 \times (17‰/1‰)^2 = 10 \times 289$ scans are to be acquired for 1‰ precision and the experimental parameters relating to the flow rate can be set accordingly. In one approach, therefore, an isotope ratio is determined with a first isotope ratio precision based on a first number of measured spectra, generally in a first experiment. Based on the first isotope ratio precision and the first number of measured spectra, for a desired second isotope ratio precision (generally better than the first isotope ratio precision) a second number of measured spectra can be determined in order to achieve the second isotope ratio precision. Subsequently, generally in a second experiment, the isotope ratio can be determined with the second isotope ratio precision using the second number of measured spectra.

The method may further comprise calibrating the at least one isotope ratio determined from the intensities of mass peaks of at least two isotopologues. The accuracy of the isotope ratio measurement can be improved by calibrating the at least one raw isotope ratio (i.e. ratio determined directly from the mass spectra) against one or more isotope ratios for one or more known standards, as known in the art. For example, by measuring one or more isotope ratios of one or more known standards on the mass spectrometer, one or more calibration factors can be obtained and then applied to the at least one raw isotope ratio to provide a calibrated isotope ratio.

The mass analysis can comprise recording the mass spectrum of the molecular species rather than only specific mass peaks. For example, using an electrostatic orbital trap mass analyzer, or FT-ICR mass analyzer, or TOF mass analyzer the mass spectrum of the molecular species of the molecular species can be recorded. With slower or scanning mass analyzers such as quadrupole mass analyzers or magnetic sector mass analyzers, or with multi-collector magnetic sector mass analyzers, only certain mass peaks may be monitored with sufficient resolution in the timescale available with the liquid phase separation technique, such as LC.

The at least one isotope ratio of the molecular species that is determined can be at least one of $^{13}C/^{12}C$, $^{14}C/^{12}C$, $^{15}N/^{14}N$, $^{2}H/^{1}H$, $^{18}O/^{16}O$, $^{17}O/^{16}O$, or $^{34}S/^{32}S$, $^{37}Cl/^{35}Cl$, $^{81}Br/^{79}Br$, $^{29}Si/^{28}Si$, $^{30}Si/^{28}Si$, etc. (or the inverse of such ratios). Determination of the ratio is generally of the ratio of the heavy to light isotope (R), such as:

$$R = \frac{\text{Heavy Isotope}}{\text{Light Isotope}} = \frac{^{13}C}{^{12}C} = \frac{^{15}N}{^{14}N} = \frac{^{18}O}{^{16}O} \text{ etc.}$$

The isotope ratio can be determined as delta notation (δ-notation). The general way of reporting stable isotope ratios from IRMS analysis is using delta notation. The δ-value is the stable isotope ratio of an unknown sample relative to a standard (i.e. reference material) of known isotope value, calculated as:

$$\delta\ [\%_o] = \frac{R_{(Sample)} - R_{(Standard)}}{R_{(Standard)}} * 1000 = \left(\frac{R_{(Sample)}}{R_{(Standard)}} - 1\right) * 1000$$

Preferably, the isotope ratio determined from the mass analysis is a corrected isotope ratio, wherein an isotope ratio measured from the mass analysis is corrected using a plot of measured isotope ratios versus correct (certified) isotope ratios (which herein also means correct δ-values) obtained from a plurality of standard or reference materials (i.e. of known correct isotope ratio or δ-value).

The isotope ratio determination in the present invention is based on the intensities, for example on comparing (i.e. finding the ratio of) the intensities, of mass peaks of isotopologues of the molecular species, in which the isotopologues have different nominal mass (typically differing by one or two nominal mass units). That is, no combustion of the sample molecular species to $CO_2$ etc. is performed. The at least one molecular species having an isotope ratio to be determined preferably has a different mass-to-charge ratio to the molecules of the mobile phase, e.g. the solvent of the mobile phase, and thus the mass spectrum recorded of the at least one molecular species is not interfered by the solvent (no isobaric interferences from the mobile phase molecules). This avoids the problem that with a combustion technique for isotope ratio analysis a mobile phase based on organic solvent, and/or including carbon containing buffers, would produce the same species of oxidation or reduction products as organic sample molecules of interest. Typically, the monoisotopic peak (for the monoisotopic isotopologue) in the mass spectrum of the at least one molecular species having an isotope ratio to be determined, e.g. the $[M+H]^+$ peak in a mass spectrum obtained from an electrospray source, can provide an isotope abundance for the particular light isotope of interest (e.g. $^{12}C$, $^{14}N$, $^{16}O$, $^{1}H$, $^{32}S$) and an A+1 peak or A+2 peak (where A is the monoisotopic mass peak) for an A+1 isotopologue or A+2 isotopologue (generally with the same charge as the monoisotopic isotopologue) can provide an isotope abundance for the particular heavy isotope of interest (e.g. $^{13}C$, $^{15}N$, $^{18}O$, $^{2}H$, $^{34}S$). The isotope ratio determination may thus comprise comparing the intensity of a monoisotopic mass peak A with an A+1 mass peak or A+2 mass peak to provide an isotope ratio of a light isotope and a heavy isotope of interest. The high resolving power of the mass spectrometer, especially a spectrometer such one comprising an ORBITRAP mass analyzer or an FT-ICR mass analyzer, has been found able to resolve a particular A+1 peak (or A+2 peak) of an isotopologue having the particular heavy isotope of interest ($^{13}C$, or $^{15}N$, or $^{18}O$, or $^{2}H$, or $^{34}S$ etc.), i.e. resolve the peak from other A+1 nominal mass peaks (or A+2 nominal mass peaks) of isotopologues having another heavy isotope. Each isotopologue mass peak used for the isotope ratio determination should preferably be resolved from at least any other mass peaks at the same nominal mass which are more than 20%, or more preferably more than 10%, or most preferably more than 5%, of the intensity of the isotopologue mass peak. For example, in an embodiment of the invention the resolved isotope peak pattern of A+1 peaks shows that a $^{13}C$ isotopologue peak can be sufficiently resolved from a $^{15}N$ isotopologue peak or $^{2}H$ peak. Further, the resolved isotope peak pattern of A+2 peaks shows that an $^{18}O$ isotopologue peak can be sufficiently resolved from a $^{13}C_2$ isotopologue peak or an $^{13}C^{15}N$ isotopologue peak. Thus, the invention enables analysis of multiply substituted isotopologues as well as singly substituted isotopologues. The mass analysis therefore preferably resolves the monoisotopic peak from A+1 and A+2 peaks. The mass analysis further preferably resolves two or more A+1 isotopologues and/or two or more A+2 isotopologues from each other. The light isotope is preferably selected from $^{12}C$, $^{14}N$, $^{16}O$, $^{1}H$, $^{32}S$, $^{35}Cl$, $^{79}Br$, $^{28}Si$ and the heavy isotope is preferably selected from $^{13}C$, $^{14}C$, $^{15}N$, $^{17}O$, $^{18}O$, $^{2}H$, $^{34}S$, $^{37}Cl$, $^{81}Br$, $^{29}Si$, $^{30}Si$. Herein, when referring to peaks at the same nominal mass, it is not meant peaks at the same nominal mass to charge ratio (m/z). For example, in a case of isotopic mass peaks due to multiply charged ions (e.g. +5 or higher, +10 or higher, . . . ) several isotopic peaks (such as A+1, A+2, A+3 peaks) will appear at the same nominal m/z (though they do not have the same nominal mass). The invention is not concerned with resolving such multiply charged isotopic peaks (with different nominal mass) from each another. Rather, the invention is concerned with resolving various isotopologues of a specific A+n group of peaks (n=1, 2, 3, . . . ), i.e. resolving peaks at the same nominal mass. Accordingly, when referring to 'peaks at the same nominal mass' this is referring effectively to a mass spectrum wherein any multiply charged peaks have been transformed to singly charged peaks. In other words, for multiply charged ions, it is not meant to resolve the A+1, A+2, A+3, . . . peaks from one another, but rather the multiple isotopologue peaks at the same A+n (A+1, A+2, A+3, . . . ) group from one another.

Preferably, the isotopologues are not isotopically labelled, i.e. they are not artificially enriched in at least one isotope. Thus, the invention is not primarily concerned with so-called isotope labelling experiments in which one sample is isotopically labelled while another sample is not and the ratio of an isotopically labelled molecular species to an unlabeled molecular species is determined, in the invention, the at least one molecular species is derived from one sample, not two or more samples as in labelling experiments. Accordingly, the isotope ratio of the molecular species that is determined is preferably a natural or inherent isotope ratio of the molecular species, i.e. not a ratio of the abundance of a labelled molecular species vs a non-labelled molecular species. The measurement of natural or inherent abundances of isotopes is used widely in environmental chemistry, geochemistry, and forensic analysis, as well as in biological, biochemical and biomedical research and applications.

The mass analysis is preferably performed with a high resolving power (R). The mass analysis is preferably performed with a sufficient resolving power (R) to resolve mass peaks of isotopologues of the at least one molecular species. The mass analysis is preferably performed with a mass resolving power high enough to resolve the two most abundant mass peaks (isotopologues of the molecular species or non-isotopologue interferences from other molecular species) at the nominal mass of at least one of the isotopologues used to determine the isotope ratio (preferably at the nominal masses of each of the isotopologues used to determine the isotope ratio). The two most abundant mass peaks that are resolved at the same nominal mass are desirably two isotopologues (since preferably the liquid separation step will ensure that other molecular species are not present having mass peaks within 2 m/z units of the isotopologues used to determine the isotope ratio). The two most abundant mass peaks at the nominal mass are preferably peaks that if not resolved would each contribute significantly to the isotope ratio to be determined (e.g. by contributing >20%, or >10%, or >5% of the peak intensity of the isotopologue at the nominal mass). The mass analysis is preferably performed with a mass resolving power high enough to resolve the two most abundant A+1 isotopologues and/or the two most abundant A+2 isotopologues (where A is the monoisotopic mass peak). The mass analysis is preferably performed with a sufficient resolving power (R) to resolve at least one of the following isotopologue pairs of the at least one molecular species: $^{13}$C and $^{12}$C isotopologues, $^{15}$N and $^{14}$N isotopologues, $^{18}$O and $^{16}$O isotopologues, $^{34}$S and $^{32}$S isotopologues. The resolving power is preferably high enough to resolve isotopologues that would otherwise significantly contribute (e.g. with more than 20%, or 10%, or 5% contribution to observed peak abundance) to the isotope ratio of interest. The mass analysis is preferably performed with a sufficient resolving power (R) to resolve A+1 peaks (where A is the monoisotopic mass peak) due to $^{13}$O isotopologues and $^{15}$N isotopologues. The mass analysis is further preferably performed with a sufficient resolving power (R) to resolve A+2 peaks due to $^{18}$O isotopologues, $^{13}$C$_2$ isotopologues and $^{13}$C$^{15}$N isotopologues. The resolving power, R, (at m/z 200) is preferably at least 50,000, at least 100,000, at least 150,000, at least 200,000, at least 250,000, at least 300,000, at least 400,000, or at least 500,000. As a trade off with acquisition time, the resolving power, R, (at m/z 200) is preferably in the range 50,000 to 400,000, or 100,000 to 400,000, more preferably 50,000 to 300,000, or 100,000 to 300,000, or even more preferably 200,000 to 300,000. In a preferred embodiment, the resolving power is high enough to resolve all isotopologues that would otherwise significantly contribute to the isotope ratio of interest (e.g. isotopologues that would have above 20%, or 10%, or 5% contribution to the observed peak abundance). However, the resolving power is desirably not significantly higher than required to resolve such isotopologues (as operating at higher resolving power generally slows down the step of mass analysis).

The method and the apparatus of the invention can provide for an isotope ratio precision (repeatability) typically of <20 δ‰ (i.e. <2 δ‰), preferably <10 δ‰ (<1 δ‰). Preferably, the flow rate is reduced to such a flow rate and/or for at least long enough that a desired isotope ratio precision is reached. Preferably, the desired isotope ratio precision is <20 δ‰, or <15 δ‰, or <10δ‰, or <7 δ‰, or <5 δ‰, or <3 δ‰, or <1 δ‰, or <0.5 or <0.1‰.

The mass spectrometer preferably comprises any suitable ionization source. Preferred ionization sources are ionization sources compatible with coupling to a liquid separation device, such as an LC column. These preferred ionization sources can be an electrospray ionization (ESI) source, nanospray ionization source, other atmospheric pressure ionization (API) source, such as atmospheric pressure chemical ionization (APCI) source. But other ionization sources can be used, such as electron impact (EI) ionization, chemical ionization (CI), etc.

The mass spectrometer preferably comprises a mass analyzer having a mass resolving power high enough to resolve at least the two most abundant mass peaks at the nominal mass of an isotopologue used to determine an isotope ratio of the molecular species having an isotope ratio to be determined. The mass resolving power is desirably high enough to resolve at least the two most abundant mass peaks at the nominal mass of each isotopologue used to determine the isotope ratio. The two most abundant mass peaks can be the mass peaks of the two most abundant isotopologues of the molecular species at the same nominal mass. The isotopologues of the molecular species at each different nominal mass used to determine the isotope ratio are preferably one of the two most abundant isotopologues at that nominal mass. The mass spectrometer can comprise one or the following types of mass analyzers: an ion trap, RF ion trap, electrostatic ion trap, electrostatic orbital trap (such as an ORBITRAP mass analyzer), Fourier transform (FTMS) analyzer, Fourier transform ion cyclotron resonance (FT-ICR) analyzer, time of flight (TOF) analyzer, linear TOF, orthogonal acceleration TOF (OA-TOF), reflectron TOF, multi-reflection TOF (MR-TOF), quadrupole mass filter, magnetic sector mass analyzer. Preferably, the mass spectrometer comprises a mass analyzer that is capable of high resolution and accurate mass (HR-AM). Preferably, the mass spectrometer comprises a mass analyzer that is capable of measuring all of the m/z of interest in one acquisition or scan. Preferred mass spectrometers comprise an electrostatic ion trap, electrostatic orbital trap (such as an ORBITRAP mass analyzer), or an FT-ICR, or a TOF such as a single-reflection or multi-reflection (MR)-TOF (preferably MR-TOF).

The mass analysis comprises ionizing the at least one molecular species in an ionization source to produce ions of the at least one molecular species followed by mass analyzing the ions using a mass analyzer. A mass spectrometer is therefore provided that comprises the ionization source and mass analyzer. The method preferably comprises mass filtering the ions downstream of the ionization source and upstream of the mass analyzer. The mass spectrometer thus preferably comprises a mass filter between the ionization source and the mass analyzer. In this way, the ions from the ion source can pass through the mass filter on route to the mass analyzer. The mass filter may select a narrow m/z window of ions for injection into the mass analyzer for mass analysis, i.e. the m/z window to include the m/z of the molecular species having an isotope ratio to be determined. This can enable the mass analyzer to be filled with a greater number of ions of the molecular species having an isotope ratio to be determined. The solvent matrix molecules preferably also can be removed from the ion stream by the mass filter operating with the narrow m/z window that includes the m/z of the molecular species to be analyzed. A preferred mass filter is a quadrupole mass filter. The narrow m/z window selected by the mass filter can be 20 amu wide or less, or 15 amu wide or less, or 10 amu wide or less. The ions of the molecular species having an isotope ratio to be determined, especially the mass filtered ions, are preferably accumulated in an ion store such as a linear ion trap, downstream, of the ion source and, where present, mass filter. The accumulated ions can then be ejected from the ion store to the mass analyzer for mass analysis. A preferred embodiment utilizes a curved linear trap (or C-Trap) as an ion store and ejecting the ions from the C-trap to an electrostatic orbital trap (such as an ORBITRAP mass analyzer) as the mass analyzer.

The determining of at least one isotope ratio of the at least one molecular species may comprise determining at least one position specific isotope ratio. The ions optionally can be fragmented before mass analysis, so that the fragments can be mass analyzed thereby to obtain position specific information can be obtained about the isotope ratios. Thus, in such embodiments, the step of determining at least one isotope ratio of the at least one molecular species can comprise determining position specific information about the determined isotope ratio. The mass spectrometer thus can comprise a fragmentation cell downstream of the ionization source, e.g. located with respect to the mass analyzer such that molecular species of interest can be fragmented and then the fragments mass analyzed. For example ions can be filtered through the mass filter, then fragmented and then the fragments mass analyzed, optionally after storing the fragments in the ion store. In this way, from the isotopic mass patterns of the fragments measured by the mass analyzer, position specific information can be obtained about the isotope ratios. The fragmentation cell can be a collision cell for collision induced dissociation (CID), or a cell for electron transfer dissociation (ETD), or electron capture dissociation (ECD), or photo-induced dissociation (PID) etc.

Through the use of the combined means for determining a position specific isotope ratio and the multiply substituted isotopologues, it will be appreciated that it is possible to analyze the molecular species to determine position specific isotope ratios of multiply substituted isotopologues.

DETAILED DESCRIPTION OF EMBODIMENTS

In order to enable a more detailed understanding of the invention, embodiments will now be described by way of examples with reference to the accompanying drawings.

Figure 1:
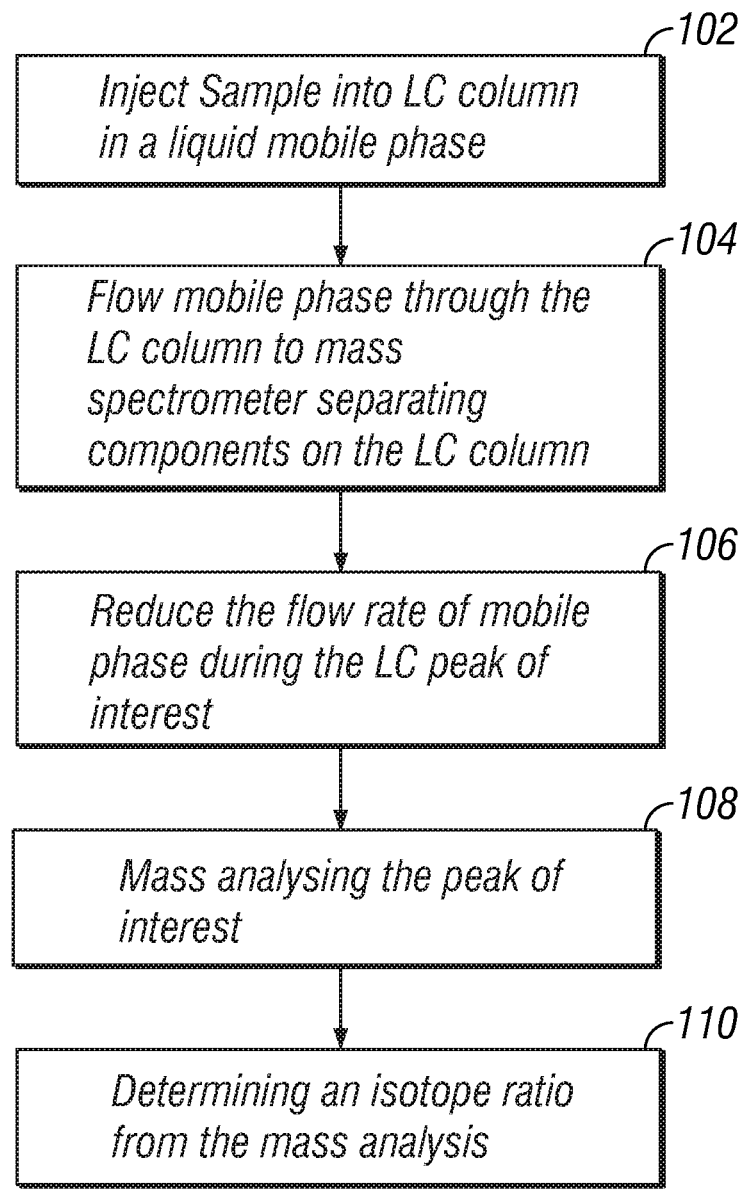
FIG. 1 shows a flow diagram schematically showing an embodiment of the invention.

Referring to FIG. 1, a method is described in relation to an LC column but it should be understood that the invention is applicable to other liquid based separation devices as described above. In a first step 102, a sample containing a number of components to be separated is injected into a liquid mobile phase in a conventional manner in an LC system. Typically, a plurality of components are to be separated. In other embodiments, a single component may be present in the sample.

Figure 2:
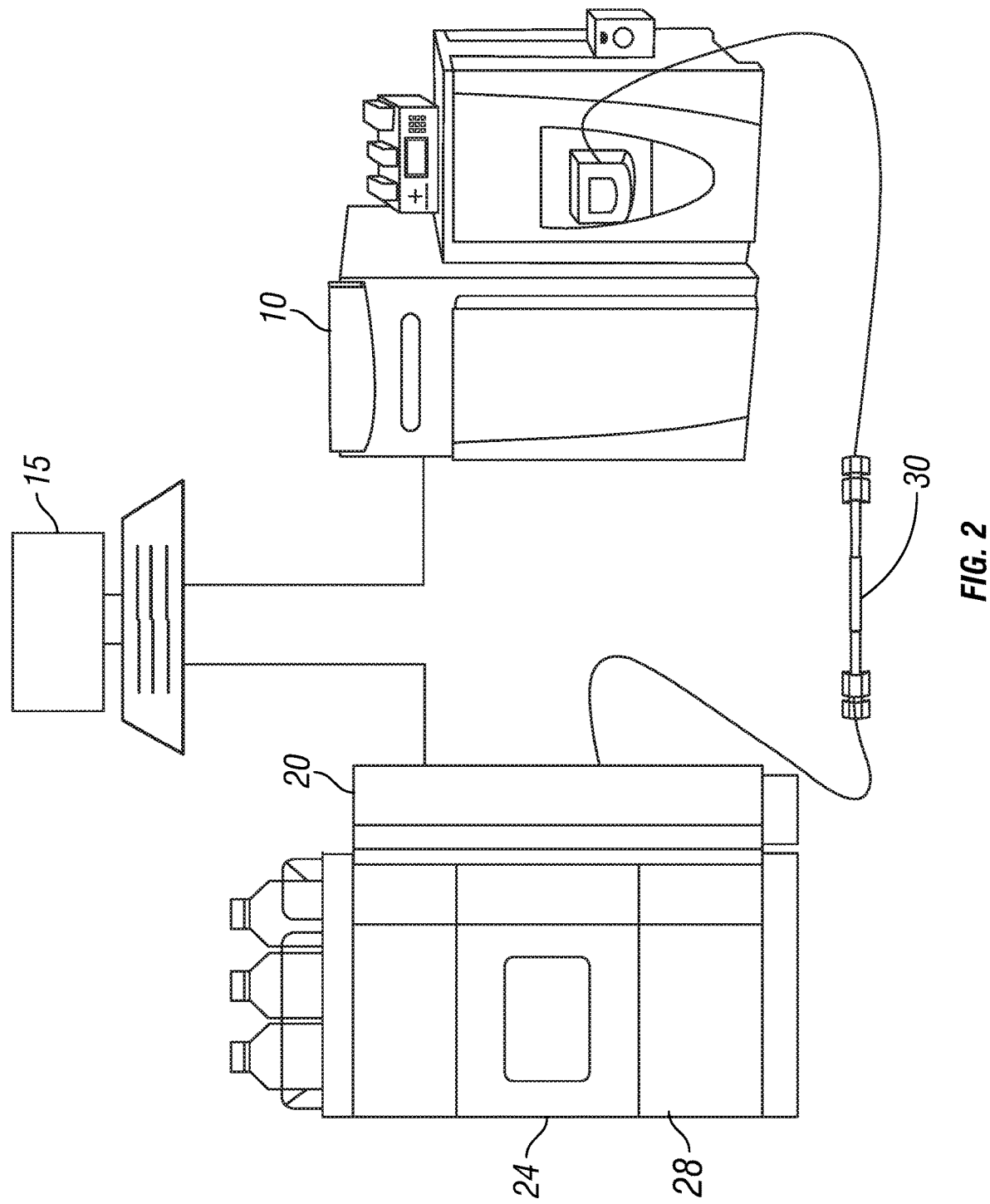
FIG. 2 shows schematically an embodiment of an apparatus for LC/MS for use in the invention.

An apparatus as shown schematically in FIG. 2 may be used. In this embodiment, a mass spectrometer 10 is interfaced to an LC system 20. The LC system includes an autosampler 24 for holding samples to be analyzed and a pump system 28 that includes at least one pump, such as a syringe pump, to drive liquid mobile phase and a sample injector to inject a sample into the mobile phase. A preferred mass spectrometer 10 is a Q Exactive® mass spectrometer from Thermo Scientific, such as the Q Exactive® HF mass spectrometer, which includes an ORBITRAP mass analyzer. A preferred LC system is a Vanquish® UHPLC system from Thermo Scientific. The mobile phase loaded with sample is pumped through the LC column 30. A preferred LC column is an Accucore aQ HPLC column, 2.1×100 mm from Thermo Scientific. The mass spectrometer 10 and LC system 20 are typically under the control of a controller 15 that includes a computer system. The controller typically handles data acquisition from the mass spectrometer and data processing of acquired data. Data processing includes the determination of isotope ratios from the mass analysis data. The controller also controls the pump system of the LC system 20, to reduce the flow rate of the mobile phase in accordance with the invention. It will appreciated that in other embodiments, the controller for the LC system or separation device could be a separate controller from a controller for the mass spectrometer.

Figure 3:
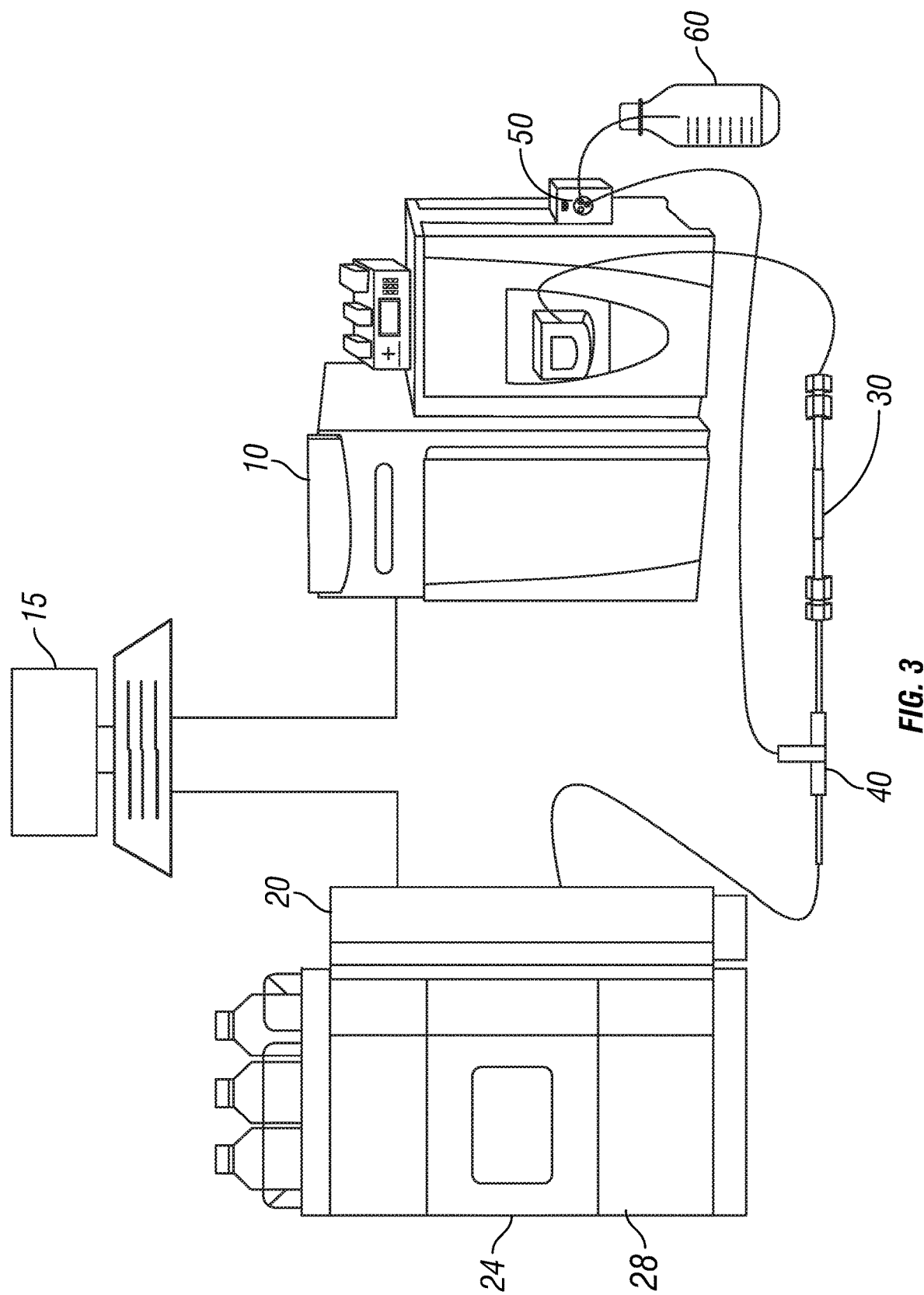
FIG. 3 shows schematically another embodiment of an apparatus for LC/MS for use in the invention.

Another apparatus for use in the invention is shown schematically in FIG. 3, described in more detail below.

The sample comprises at least one component that is a molecular species having an isotope ratio to be determined. The mobile phase will typically comprise an organic solvent. If a gradient solvent is used, at least a part of the gradient will typically comprise an organic solvent. However, in other embodiments, aqueous-based, even fully aqueous, mobile phase could be used.

In step 104, using the pump system the mobile phase is flowed through the LC column by a means of the pump to the mass spectrometer and one or more of the components of the sample become separated by the LC column as they elute from the column with different retention times. The eluate and mobile phase leaving the column flow to the downstream mass spectrometer for detection. In another type of embodiment, components eluting from the LC column can be collected and/or stored in one or more separate compartments and subsequently analyzed offline (e.g. in a separate mass spectrometer offline). For example, LC sample collection could be made in well plates and later analyzed by an MS by infusion or electrospray or nanospray.

In preferred embodiments, the mass spectrometer is able to analyze in one acquisition cycle the full mass spectrum of each of the components eluting from the column, i.e. all mass (m/z) peaks of a compound can be recorded in a single acquisition cycle. Spectrometers that comprise high resolution and accurate mass (HR-AM) analyzers are preferred. Preferred spectrometers include mass analyzers of the following types, Fourier transform (FT) mass analyzers, electrostatic orbital traps (such as an ORBITRAP mass analyzer) which are typically FT, FT-ICR mass analyzers, and single or multi-reflection TOF mass analyzers. In such analyzers, all mass (m/z) peaks of a compound are measured during one acquisition cycle (herein referred to as measurement 'in parallel'), i.e. from a single injection of ions into the analyzer.

The mass spectrometer typically analyses the eluate over time, e.g. at set sampling intervals, to provide a mass chromatogram, i.e. a series of mass spectra measured at a series of data points across retention time. In step 106, the flow rate of the liquid mobile phase flowing through the LC column is reduced for at least a portion of the time that the molecular species having an isotope ratio to be determined emerges from the column. The flow rate in the preferred embodiment is reduced just before the molecular species of interest starts emerging from the column (e.g. at a time starting from between 1 and 100 secs before, more preferably between 1 and 50 secs before and even more preferably between 1 and 10 secs before). The rate remains reduced until at least a time when most of the molecular species has emerged from the column, such as until a time when the molecular species has substantially finished emerging from the column, or preferably until the desired precision in the isotope ratio determination has been achieved. The flow rate can remain reduced until a time after all of the molecular species has emerged from the column. The flow rate is typically reduced by a factor of at least 3, or better still at least 5 or better still at least 10, or at least 100 in some instances. The reduction factor typically has a dependence on the column size (diameter) as described above. A reduced flow rate by a factor of between 5 and 1000, or between 5 and 200, is typically employed. After the flow has been reduced in this way, the flow rate can be increased, typically to the original flow rate before the flow rate was reduced. The time at which to reduce the flow rate can be determined from a previous measurement (i.e. previous LC experiment), or it may be known from a database, or may be known a priori. Alternatively, the time at which to reduce the flow rate can be triggered by the detection of one or more mass spectral peaks of the molecular species of interest in real time as the mass spectrometer analyses the eluting species.

The reduction of the flow rate can be achieved in different ways. In one preferred embodiment, the speed of the pump (i.e. the pressure of the pumping) that drives the flow of mobile phase through the column is reduced. In another preferred embodiment, the flow can be split upstream of the column by activating a valve so that a portion of the mobile phase flow is diverted into a branch flow path upstream of the separation device and only a portion is passed through the column, thus providing a reduced flow rate through the column. Such a system is shown schematically in FIG. 3. In FIG. 3, the system components are generally similar to FIG. 2 so that like reference numerals denote like components. However, in the FIG. 3 set-up, a tee junction 40 has been inserted into the flow path upstream of the LC column and connected to a HPLC switching valve 50. The valve can be switched between two positions: i) a blocked port, and ii) a port connected to a flow restriction capillary leading to a waste receiver 60. If the valve is switched to position i), all of the flow goes through the column. However, when the valve is switched to position ii), only a fraction of the flow goes through the column (e.g. 10%), thereby extending the time it takes to elute a peak from the column and leading to significant peak broadening. The switching valve 50 is under the control of the controller 15.

In step 108, at a point during the sample elution, the mass spectrometer records the mass spectrum of the peak of interest from the LC column corresponding to at least the molecular species having an isotope ratio to be determined. As mentioned, the mass spectrometer records the mass spectrum of the eluate as it emerges from the LC column in a sequence of data acquisition cycles taken over time. The mass spectrum is typically recorded across the range of retention times from 0 minutes (or sample injection) until at least the mass spectrum of the molecular species having an isotope ratio to be determined has been recorded across its elution peak. As described, the flow rate is reduced during the period of the elution peak of interest, which increases the peak width (or elution time, i.e. the time it spends in the eluate) for the molecular species having an isotope ratio to be determined. Thus, the total mass analysis time for the molecular species having an isotope ratio to be determined is extended by the reduction in flow rate, i.e. by increasing the number of measurement points by a factor of the ratio of the peak widths (peak width with flow reduction/peak width without flow reduction). For many of the preferred ionization methods employed in the mass spectrometer when coupling to a liquid separation like LC, such as an electrospray ionization method, the signal intensity is not significantly affected by the reduction in flow rate. Thus, the overall result is a gain in precision of the mass spectrum. Preferably, the isotope ratio precision is <20 δ‰, preferably (in order of increasing preference) <15 δ‰, or <10 δ‰, or <7 δ‰, or <5 δ‰, or <3 δ‰, or <1 δ‰, or <0.5 δ‰, or <0.1‰.

The mass spectrum recorded includes an isotopic pattern from which it is possible to resolve a plurality of isotopic peaks, i.e. peaks due to different isotopologues of the molecular species having an isotope ratio to be determined. From analysis of the isotopically resolved mass spectrum, an isotope ratio can be determined (step 110). For example, from intensities of two or more resolved isotopic peaks in the mass spectrum, often where one is the monoisotopic peak, it is possible to determine an isotope ratio (optionally expressed as a delta (δ) value) for an element. Preferred elements of interest to determine an isotopic ratio for are C, N, O, H, S, P, Cl, Br and Si. Some common isotope ratios to be determined include $^{13}C/^{12}C$, $^{14}C/^{12}C$, $^{15}N/^{14}N$, $^{2}H/^{1}H$, $^{18}O/^{16}O$, $^{17}O/^{16}O$ or $^{34}S/^{32}S$, $^{37}Cl/^{35}Cl$, $^{81}Br/^{79}Br$, $^{29}Si/^{28}Si$, $^{30}Si$, $^{28}Si$, etc.

The isotope ratio determination in the present invention can be based on the intensities, for example on comparing (i.e. finding the ratio of) the intensities, of mass peaks of isotopologues of the molecular species, in which the isotopologues have different nominal mass (typically differing by one or two nominal mass units). Typically, the monoisotopic peak (for the monoisotopic isotopologue) in the mass spectrum of the at least one molecular species having an isotope ratio to be determined, e.g. the $[M+H]^+$ peak in a mass spectrum obtained from an electrospray source, can provide an isotope abundance for the particular light isotope of interest (e.g. $^{12}C$, $^{14}N$, $^{16}O$, $^{1}H$, $^{32}S$) and an A+1 peak or A+2 peak (where A is the monoisotopic mass peak) for an A+1 isotopologue or A+2 isotopologue can provide an isotope abundance for the particular heavy isotope of interest (e.g. $^{13}C$, $^{15}N$, $^{18}O$, $^{2}H$, $^{34}S$). The isotope ratio determination may thus comprise comparing the intensity of a monoisotopic mass peak A with an A+1 mass peak or A+2 mass peak to provide an isotope ratio of a light isotope and a heavy isotope of interest. The high resolving power of the mass spectrometer, especially a spectrometer comprising an ORBITRAP mass analyzer, has been found able to resolve a particular A+1 peak (or A+2 peak) of an isotopologue having the particular heavy isotope of interest ($^{13}C$, or $^{15}N$, or $^{18}O$, or $^{2}H$, or $^{34}S$ etc.), i.e. resolve that particular isotopologue peak from other A+1 nominal mass peaks (or A+2 nominal mass peaks) of isotopologues having another heavy isotope. Each isotopologue mass peak used for the isotope ratio determination should preferably be resolved from at least any other mass peaks at the same nominal mass which are more than 20%, or more preferably more than 10%, or most preferably more than 5%, of the intensity of the isotopologue mass peak. For example, in an embodiment of the invention the resolved isotope peak pattern of A+1 peaks shows that a $^{13}$C isotopologue peak can be sufficiently resolved from a $^{15}$N isotopologue peak or $^{2}$H peak. Further, the resolved isotope peak pattern of A+2 peaks shows that an $^{18}$O isotopologue peak can be sufficiently resolved from a $^{13}$C$_2$ isotopologue peak or a $^{13}$C$^{15}$N isotopologue peak. Thus, the invention enables analysis of multiply substituted isotopologues as well as singly substituted isotopologues. The mass analysis therefore preferably resolves the monoisotopic peak from A+1 and A+2 peaks. The mass analysis further preferably resolves two or more A+1 isotopologues and/or two or more A+2 isotopologues from each other.

In some embodiments, the isotope ratio determination in the present invention can be based on the intensities, for example on comparing (i.e. finding the ratio of) the intensities, of mass peaks of isotopologues of the molecular species, in which the isotopologues have the same nominal mass. For example, the isotope ratio determination can be based on a ratio of the $^{15}$N isotopologue peak to the $^{13}$C isotopologue peak.

The mass analysis is preferably performed with a sufficient resolving power (R) to resolve mass peaks of isotopologues of the at least one molecular species, for example to resolve the two most abundant mass peaks at the nominal mass of at least one of the isotopologues used to determine the isotope ratio (preferably at the nominal masses of each of the isotopologues used to determine the isotope ratio). The two most abundant mass peaks that are resolved at the same nominal mass are typically two isotopologues (since the liquid separation step will typically mean that other molecular species are not present having mass peaks within 2 m/z units of the isotopologues used to determine the isotope ratio). The two most abundant mass peaks at the nominal mass are preferably peaks that if not resolved would each contribute significantly to the isotope ratio to be determined (e.g. by contributing >20%, or >10%, or >5% of the peak intensity of the isotopologue at the nominal mass). The mass analysis is preferably performed with a mass resolving power high enough to resolve the two most abundant A+1 isotopologues and/or the two most abundant A+2 isotopologues (where A is the monoisotopic mass peak).

Figure 14:
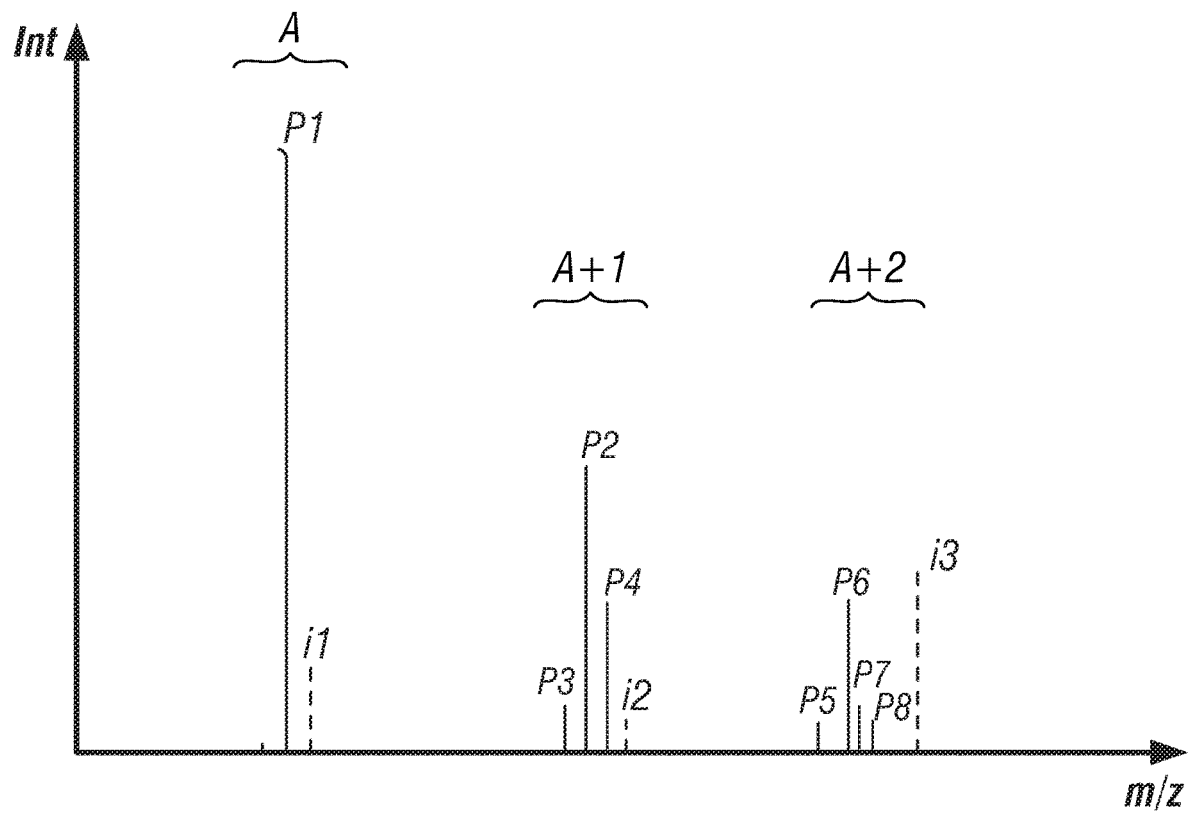
FIG. 14 shows a schematic mass spectrum displaying an isotopic mass peak pattern of isotopologues of an eluting molecular species. The solid lines represent mass peaks of isotopologues of the same molecular species whose isotope ratio is to be determined. The dotted lines represent mass peaks of external interferences.
Figure 15:
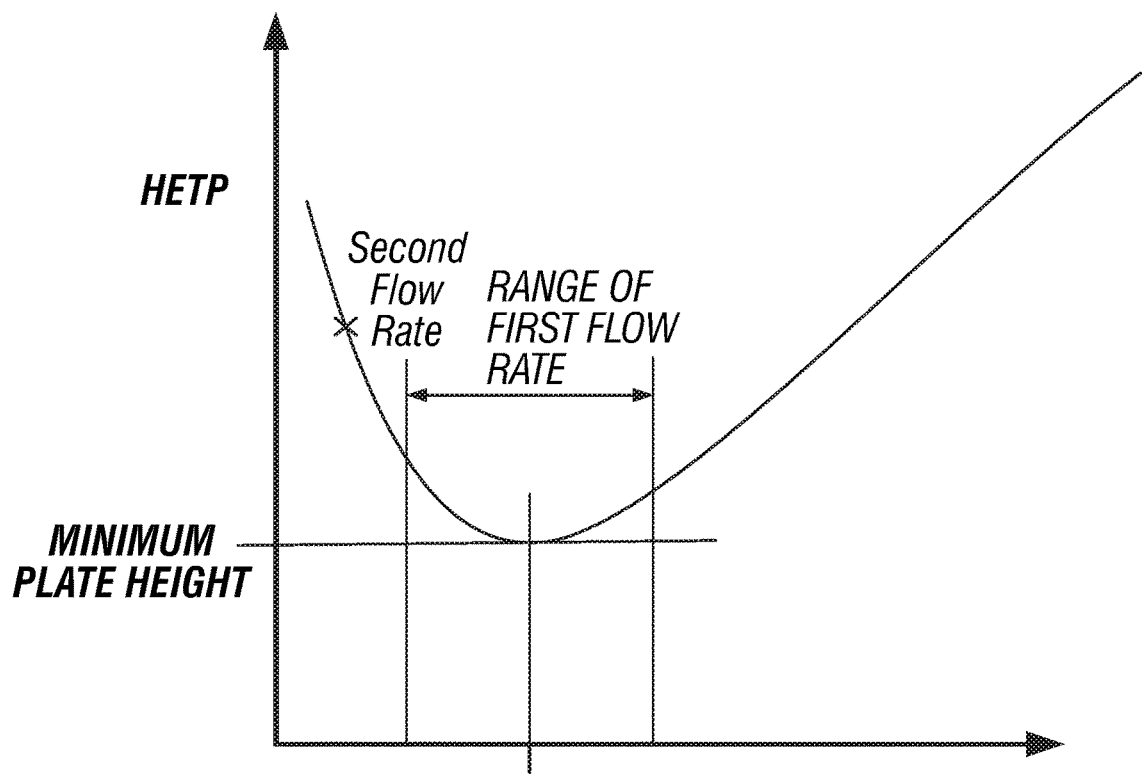
FIG. 15 shows a schematic relationship between HETP and the flow rate for an HPLC column.

Referring to FIG. 14, there is shown a schematic mass spectrum displaying an isotopic mass peak pattern of isotopologues of an eluting molecular species. The solid lines represent mass peaks of isotopologues of the same molecular species whose isotope ratio is to be determined. The dotted lines represent mass peaks of external interferences from other molecular species. A monoisotopic peak P1 of nominal mass A is shown, which is resolved from a small external interference mass peak i1 at the same nominal mass A. An isotopologue peak P2 is also indicated at nominal mass A+1, which is to be used together with the monoisotopic peak P1 to find an isotope ratio of the molecular species, i.e. the ratio of the intensity of the P2 (A+1) peak to the P1 (A) peak, which can be expressed as a delta value. The P2 A+1 isotopologue peak is resolved from two other A+1 isotopologue peaks P3 and P4 as well as an external interference peak i2. It can be seen that at least the two most abundant A+1 mass peaks, P2 and P4, are mass resolved from each other. It is particularly important that P2 is resolved from P4 since P4 is more than 20% of the intensity of the P2 peak and so would significantly affect the isotope ratio determination. It is also preferable that P2 is resolved from P3 since P3 is more than 10% of the intensity of the P2 peak. As an example, the A+1 peak, P2, could be the $^{13}$C isotopologue and together with the monoisotopic peak P1 could be used to determine the $^{13}$C/$^{12}$C ratio. In addition, the A+1 peak, P3, could be the $^{15}$N isotopologue and together with the monoisotopic peak P1 could be used to determine the $^{15}$N/$^{14}$N ratio. Similarly, with the A+2 nominal mass peaks, there are shown isotopologue peaks P5, P6, P7 and P8 and an external interference peak i3, which are all mass resolved from each other and may be used with the monoisotopic peak P1 to determine isotope ratios, e.g. of isotopes differing by two nominal mass units such as $^{34}$S/$^{32}$S, or $^{18}$O/$^{16}$O, or of multiply substituted isotopologues such as $^{13}$C$_2$ or $^{13}$C$^{15}$N. Importantly, at least the two most abundant A+2 mass peaks, P6 and i3, are mass resolved from each other.

Different work flows can be used for determining the isotope ratio from the mass spectrum. An example of one work flow for determining the isotope ratio from the mass spectrum is given by the following steps.

1. For each spectrum acquired (this includes those spectra at retention times where no peak is eluting from the column) determine the peak intensities of the two isotope peaks of interest. This is typically done by taking the highest intensity point within a narrow mass window around the accurate mass of the peak of interest. For mass analyzers other than FT based, peak integration may the method of choice instead of height of the peak.
2. Optional step: Determine the average background intensity of the two mass peaks in an area of the chromatogram where no peak of interest and no peaks interfering with the masses of interest elute. This may be an average, geometrical average, or any other similar method of determining such a value. This step may include outlier analysis and removal. This step may include other steps (like drift testing) to make sure selected part of the chromatogram is suitable for background determination.
3. Optional step: For each spectrum across the eluted peak, subtract the average background intensities from the peaks of interest.
4. For each spectrum, determine the isotope ratio by dividing the intensity of the first (optionally background subtracted) isotope peak of interest by the intensity of the other peak of interest.
5. Optional step: Use statistical tools to validate and improve the determined ratios. For example: i) analyze and remove outliers, ii) determine whether there is any time trend (instrumental drift) in the data, iii) plot the ratios vs. peak intensities to eliminate any dependency on peak intensity, etc.
6. Determine the average isotope ratio and the standard error associated with the data set based on the data set obtained from step 4 (or optionally from step 5).

In an alternative mode of data evaluation, the spectra could be averaged first, then background subtracted and final isotope ratio be determined as the ratio of the two peaks of interest in the averaged spectrum.

EXPERIMENTAL EXAMPLES

A number of experimental examples, non-limiting on the scope of the invention, will now be described to aid understanding of the invention.

Sample and Reference Materials

Caffeine was used as a model compound to demonstrate the effectiveness of the invention. Three certified isotopic reference materials of caffeine were obtained from USGS: USGS61, USGS62, USGS63 (Schimmelmann, A., Qi, H., Coplen, T. B., Brand, W. A., Fong, J., Meier-Augenstein, W., Kemp, H. F., Toman, B., Ackermann, A., Assonov, S. and Aerts-Bijma, A. T., 2016. Organic Reference Materials for Hydrogen, Carbon, and Nitrogen Stable Isotope-Ratio Measurements: Caffeines, n-Alkanes, Fatty Acid Methyl Esters, Glycines, I-Valines, Polyethylenes, and Oils. Analytical chemistry, 88(8), pp. 4294-4302). An additional caffeine sample was obtained from Sigma Aldrich® (Sigma Aldrich® C-8960, Lot #30K0169) and characterized using a Delta V mass spectrometer couples to an EA Isolink elemental analyzer. The certified $\delta\ ^{13}C$ reference values (for USGS61-63) and measured value (for the sample from Sigma Aldrich®, herein denoted BRE001) are listed in Table 1.

TABLE 1

Certified reference values and measured values for $\delta\ ^{13}C$

| Sample Name | $\delta\ ^{13}C$ [‰] |
|---|---|
| USGS61 | −35.05 |
| USGS62 | −14.97 |
| USGS63 | −1.17 |
| BRE001 | −39.21 |

Example 1—Infusion Measurements (Comparative Example)

Figure 4:
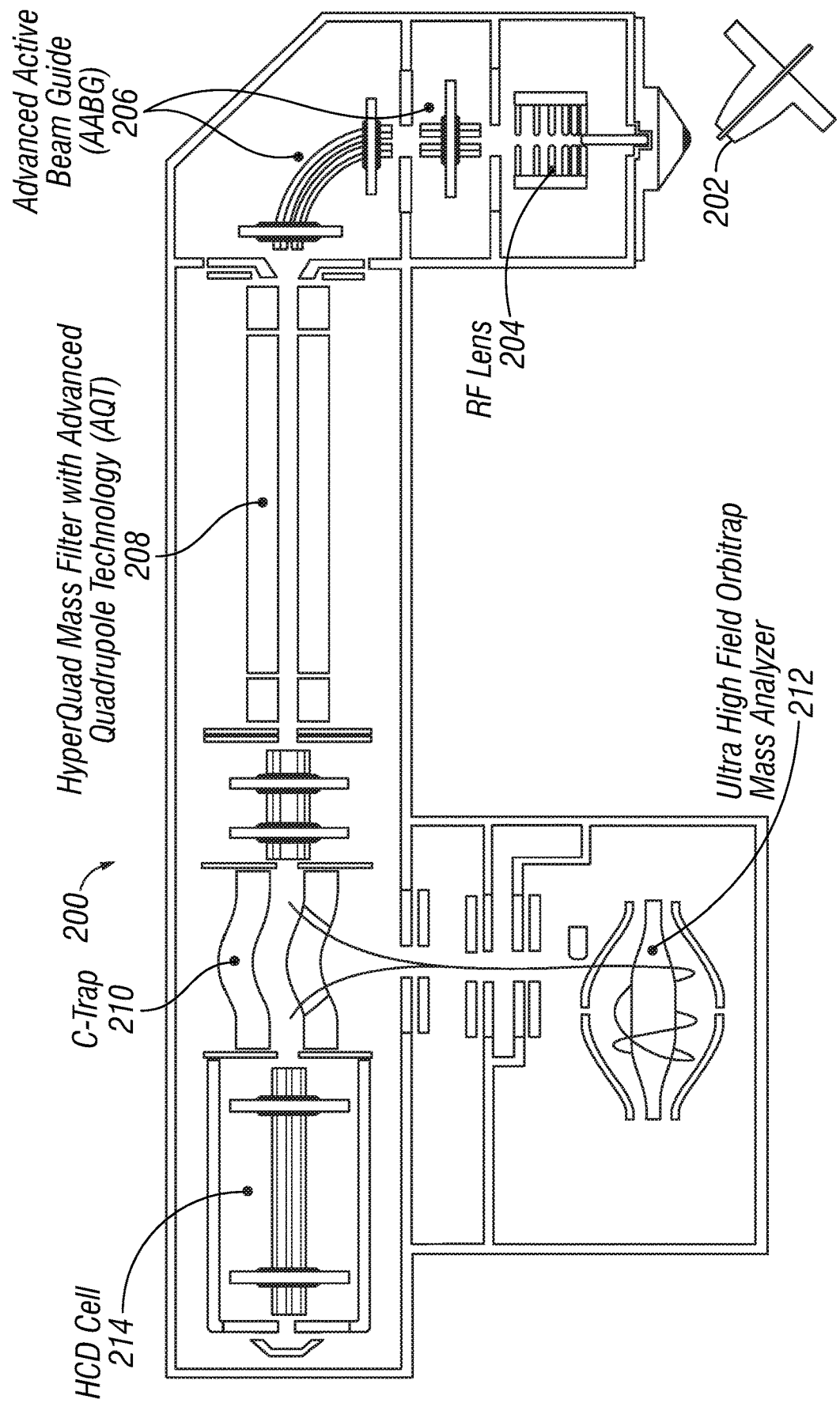
FIG. 4 shows schematically an embodiment of a mass spectrometer instrument for use in the invention.

Sample solutions of approx. 10 µg/ml of the samples listed in table 1 in methanol/water 50:50 (v:v) were made and directly infused into a standard Thermo Scientific Q Exactive® HF ORBITRAP mass spectrometer from Thermo Fisher Scientific. A schematic of the instrument, which is a preferred mass spectrometer for use in the invention, is shown in FIG. 4. The mass spectrometer 200, comprises an electrospray ion source 202 which generates ions that enter an RF lens 204 before being guided by the active beam guide ion optics 206 to a quadrupole mass filter 208. A mass isolation window can be set by the mass filter to transmit ions of the desired mass to a downstream ion trap (C-Trap) 210, where ions can be accumulated before ejection of the ions to the ORBITRAP mass analyzer 212 for mass analysis. If required, the ions can be transmitted through the C-trap 210 to a downstream higher energy collision dissociation (HCD) cell 214 where ions can be fragmented before being returned to the C-trap 210 and subsequently mass analyzed in the ORBITRAP mass analyzer 212.

The spectrometer was operated using the following parameters:
  Infusion using a syringe pump
  Mass isolation range of the spectrometer 190-200 m/z
  Resolving power=240 k @ m/z 200
  10 microscans were utilised, i.e. 10 scans in the ORBITRAP mass analyzer were performed for each transient subjected to Fourier transformation
  Target AGC value 1E6
  15 min total data acquisition, which results in approx. 160 scans per data file (with 10 microscans utilized per scan).

Figure 5:
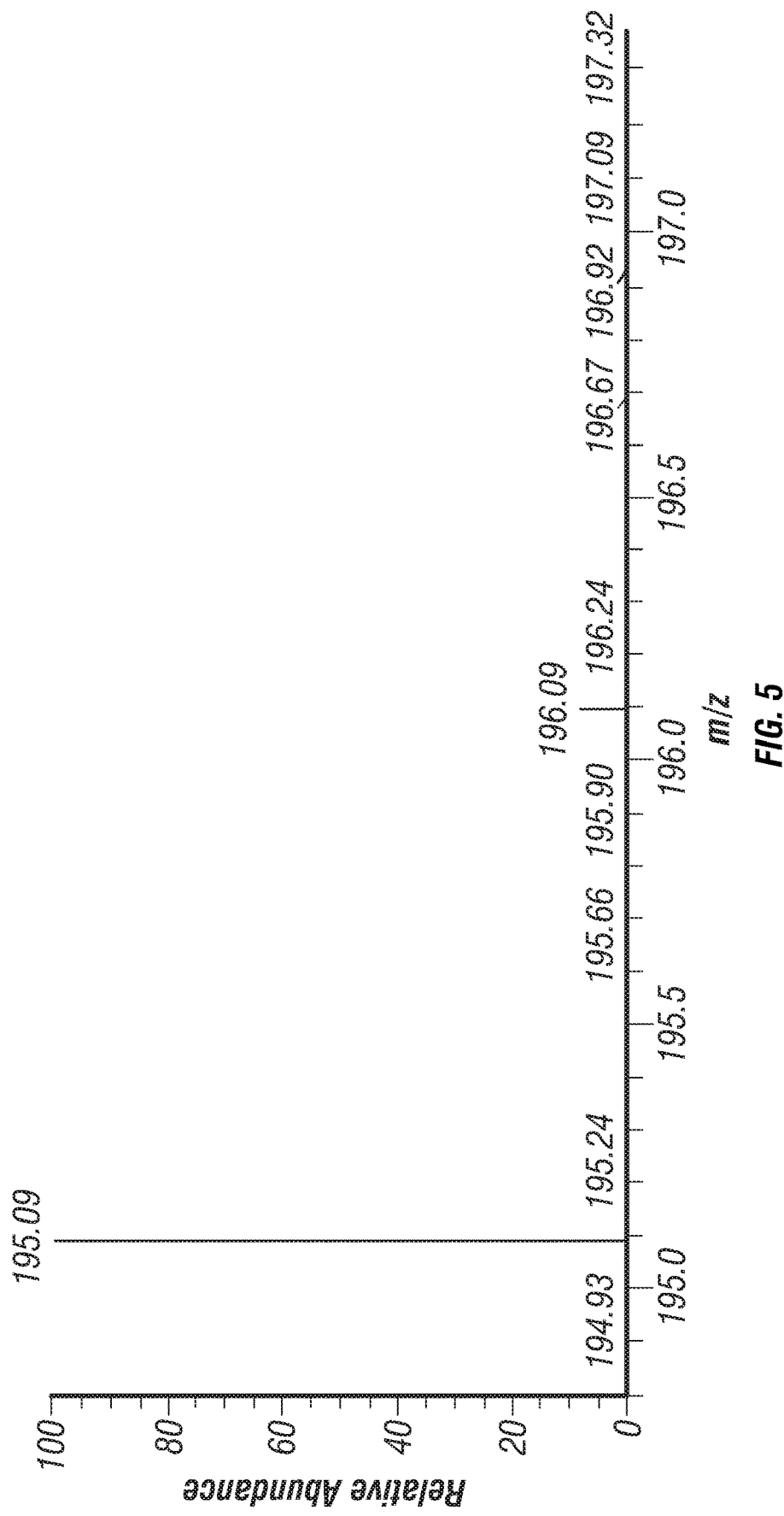
FIG. 5 shows a representative mass spectrum obtained from a sample of caffeine in an infusion MS experiment.
Figure 6:
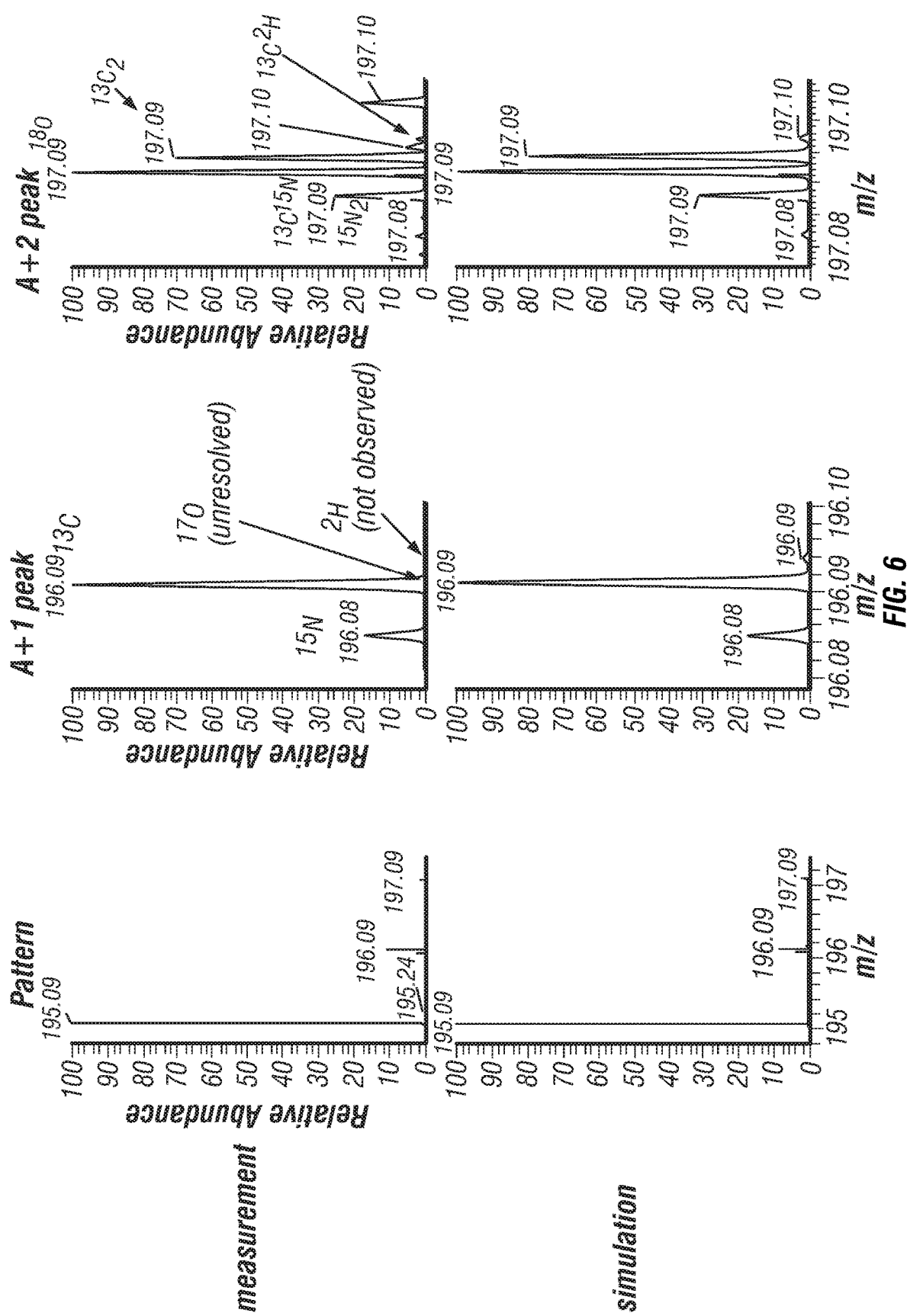
FIG. 6 shows a measured and simulated isotope pattern of caffeine.

FIG. 5 shows a representative mass spectrum obtained from the BRE001 sample of caffeine infused to the Q Exactive® HF mass spectrometer. The monoisotopic caffeine peak corresponding to the [M+H]$^+$ ion is labelled at 195.09 and an A+1 peak at 196.09. Due to the high resolution of the instrument, a closer look at the mass spectrum of the isotope peaks shows that the $^{13}C$ isotope peak at 196.09 is well resolved from the $^{15}N$ isotope peak at 196.08, but not from the $^{17}O$ isotope peak as shown in FIG. 6. However, the natural abundance of $^{17}O$ is negligible compared to the variations in $^{13}C$ abundance, such that this is quite acceptable for the study.

The top row of spectra in FIG. 6 show the measured isotope pattern of caffeine and demonstrate the resolving power. The lower row of spectra represent a simulation of the spectra of caffeine to show the good correspondence with the measured data. The peak annotations in FIG. 6 indicate the type of caffeine isotopologue (e.g. 15N, 13C, 13C2, etc.).

Figure 7:
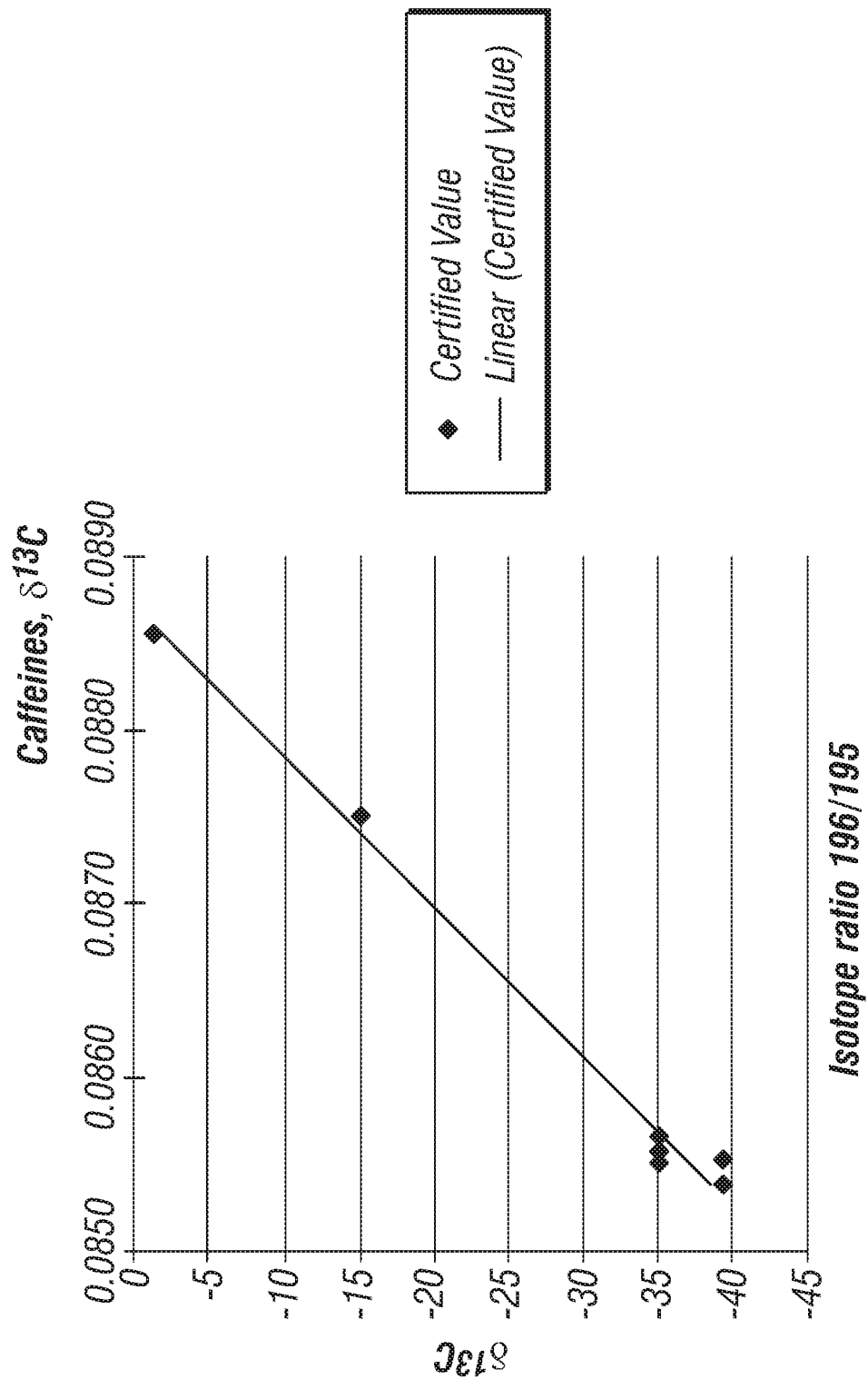
FIG. 7 shows a plot of measured isotope ratios (196/195) of vs. known certified $\delta\ ^{13}C$ values caffeine from an infusion MS experiment.

All of the samples were measured sequentially using a standard/sample bracketing sequence with USGS61 as the bracketing standard. Table 2 shows the results of the measurements with the standard denoted as Type STD and each of the samples denoted as Type UNK. FIG. 7 shows the plot of the measured isotope ratios (196/195) vs. the known certified $\delta\ ^{13}C$ values and also shows the linear calibration curve. The standard error of each single measurement in the infusion experiment was approximately 0.5-0.6% and the accuracy of the method was approx. 2-2.5‰.

TABLE 2

| Sequence | Sample | Type | Ratio (measured) | $\delta^{13}C$ (‰) Certified Value | $\delta^{13}C$ (‰) (calculated) |
|---|---|---|---|---|---|
| 1 | BRE001 | UNK | 0.0853857 | −39.21 | −36.47 |
| 2 | USGS61 | STD | 0.0855069 | −35.05 | |
| 3 | BRE001 | UNK | 0.0855094 | −39.21 | −35.34 |
| 4 | USGS61 | STD | 0.0855632 | −35.05 | |
| 5 | USGS62 | UNK | 0.0874976 | −14.97 | −12.08 |
| 6 | USGS61 | STD | 0.0855020 | −35.05 | |
| 7 | USGS63 | UNK | 0.0885502 | −1.17 | −0.29 |
| 8 | USGS61 | STD | 0.0856490 | −35.05 | |
| 9 | BRE001 | UNK | 00855340 | −39.21 | −36.39 |

Example 2—LC/MS Measurements without Reduced Flow (Comparative Example)

Figure 8:
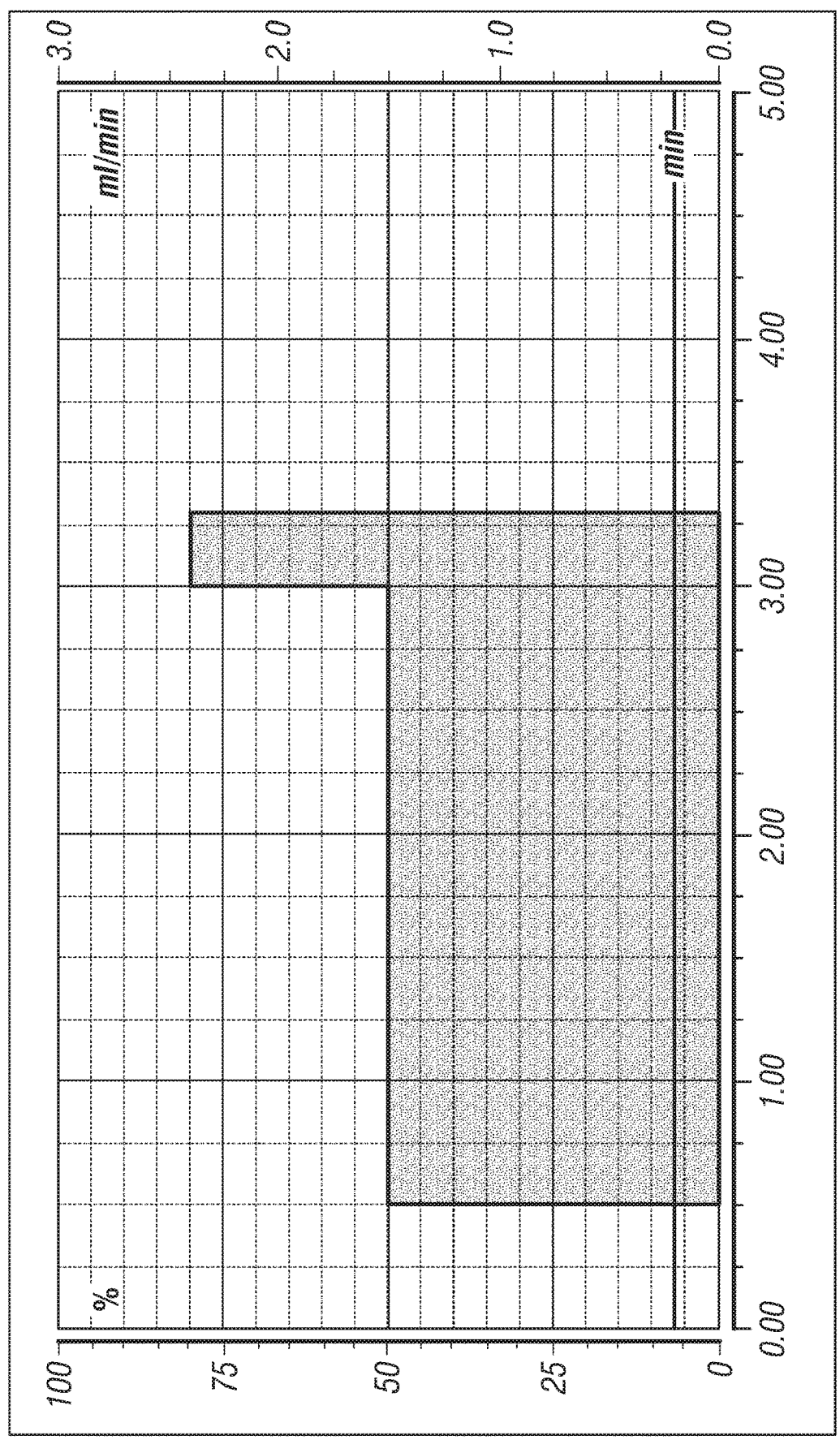
FIG. 8 shows a solvent step gradient used in an LC/MS comparative experiment.

Sample solutions of 10 µg/ml (+/−0.02 µg/ml) of the samples listed in table 1 in methanol/water 20:80 were used in the experiment. An LC/MS system as shown schematically in FIG. 2 was used with the following LC setup:
  Thermo Fisher Scientific Vanquish® LC system with autosampler and quaternary pump
  10 µl injection (corresponds to 100 ng injected)
  Thermo Fisher Scientific Accucore aQ column; 2.1×100 mm, 2.6 mm particle size
  Solvent A: water, 0.1% formic acid (FA), 2 mM ammonium acetate
  Solvent B: methanol, 0.1% FA, 2 mM ammonium acetate
  Solvent Gradient 100% A (0-0.5 min); 50% A/50% B (0.5-3.0 min); 20% A/80% B (3.0-3.3 min); 100% A (3.3-5 min). FIG. 8 shows the solvent step gradient used in the experiment.

Figure 9:
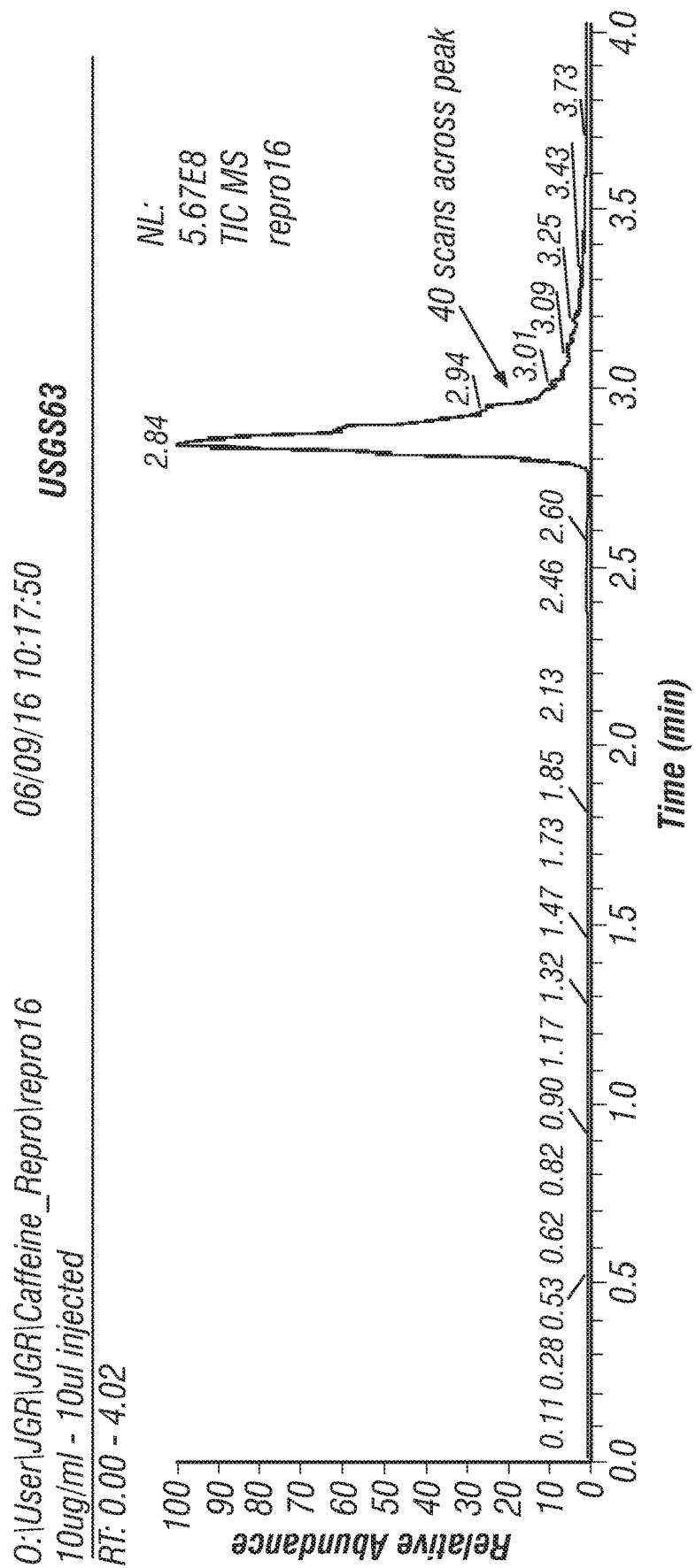
FIG. 9 shows a chromatogram and mass spectrum obtained in an LC/MS comparative experiment.
Figure 9:
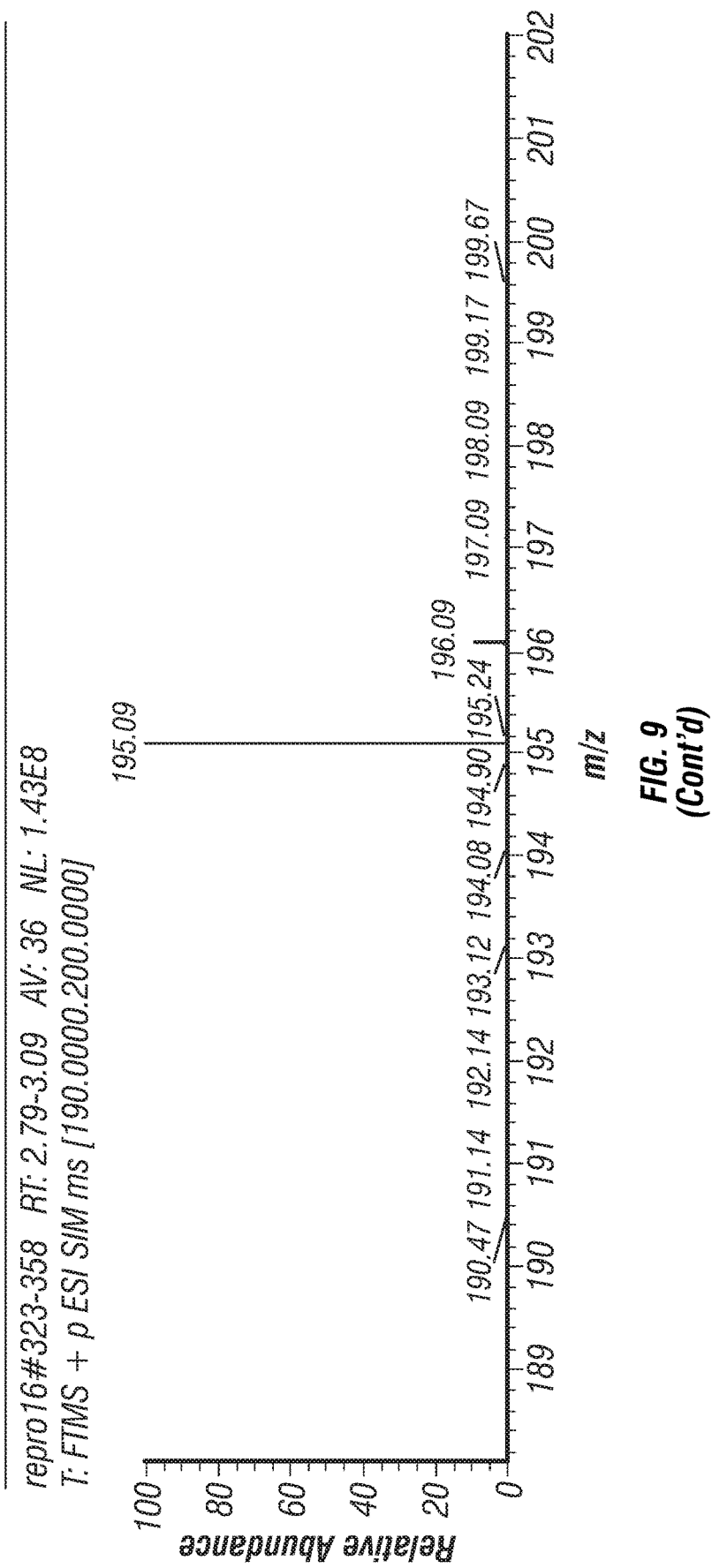
Figure 10:
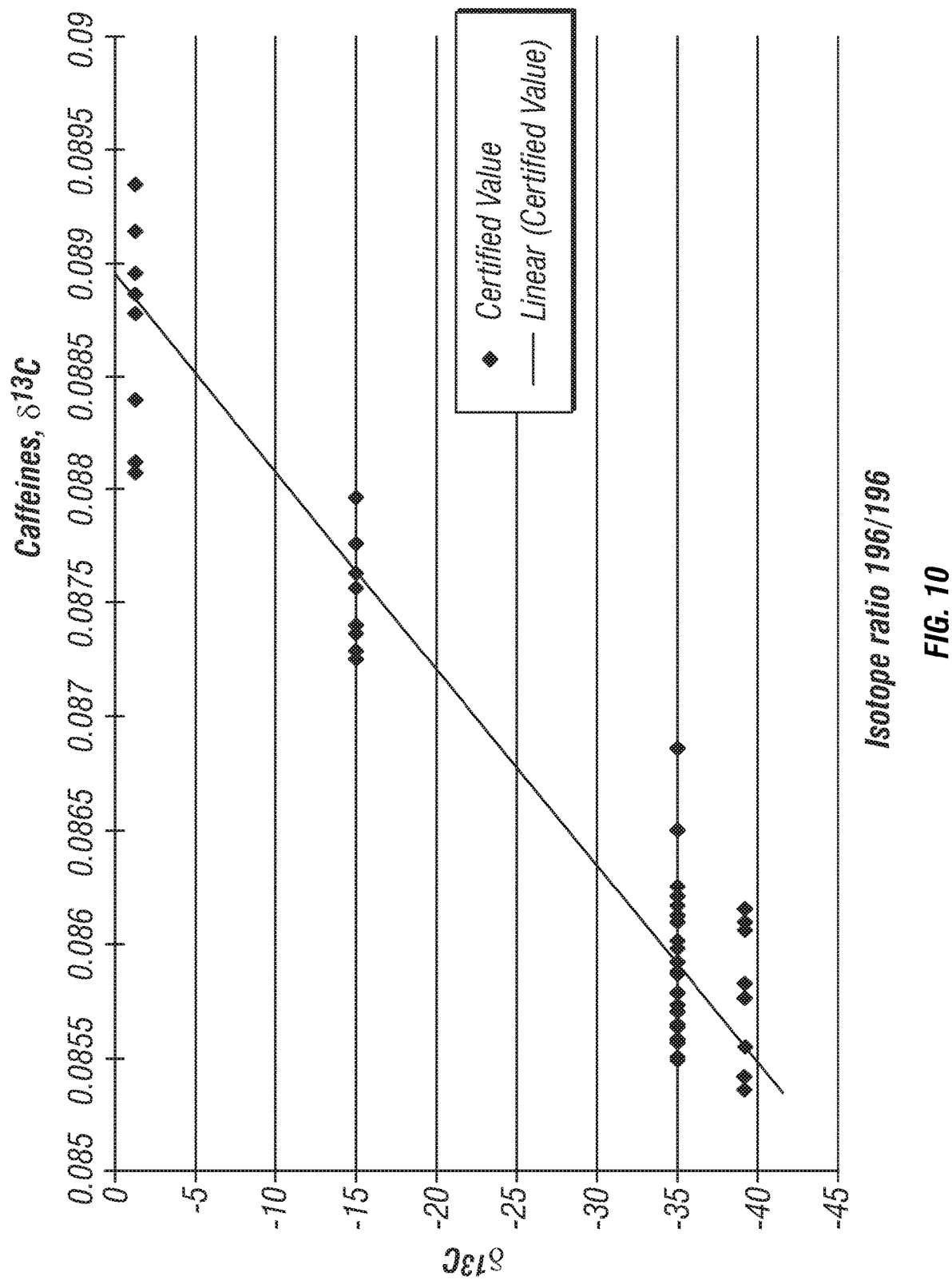
FIG. 10 shows a plot of measured isotope ratios of caffeine vs. known certified $\delta\ ^{13}C$ values from a comparative LC/MS experiment.

The mass spectrometer was operated using the following parameters:
  Mass scan/isolation range 190-200 m/z
  Resolving power=240 k @ m/z 200
  1 microscan per transient processed
  Target AGC value 1E6
  4 min total data acquisition The acquisition and data evaluation strategy employed the following:
Sample/standard bracketing
USGS1 as the reference/standard
8 repetitions of the bracketing set (49 injections in total)
Data evaluation used USGS1 measurements to correct drift
Direct calculation of δ values with no additional corrections FIG. 9 shows a typical chromatogram and mass spectrum. With the LC peak width of caffeine of approx. 0.5 min, this resulted in approx. 40 scans across the LC peak. Table 3 shows the results of the measurements and FIG. 10 shows the plot of the measured isotope ratios vs. the known certified $\delta$ $^{13}C$ values together with the linear calibration curve. The standard error of each single measurement was approximately 4-6‰. Accuracy of the method was approx. 5‰.

TABLE 3

| Sample | $\delta^{13}C$ (‰) (measured) | StdErr (‰) | Stdev (‰) | $\delta^{13}C$ (‰) Certified Value |
|---|---|---|---|---|
| USGS61 | −35.05 | N/A | N/A | −35.05 |
| USGS62 | −17.44 | 1.72 | 4.85 | −14.97 |
| USGS63 | −1.56 | 1.59 | 4.51 | −1.17 |
| BRE001 | −37.14 | 0.58 | 1.65 | −39.21 |

Example 3—LC/MS Measurements with Reduced Flow

Figure 11:
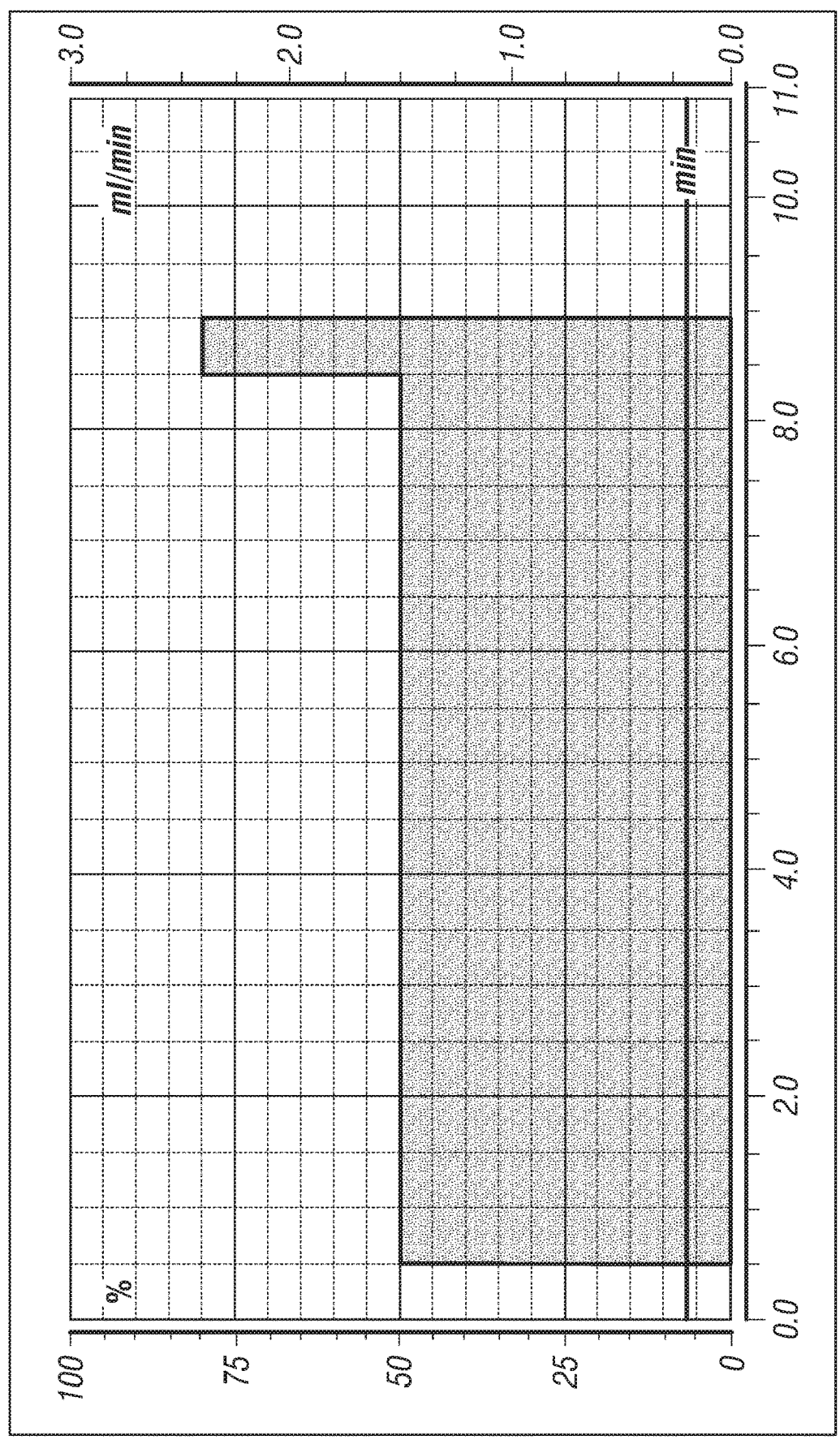
FIG. 11 shows a solvent step gradient used in an LC/MS experiment with a reduced flow step.

Sample solutions of 10 μg/ml (+/−0.02 μg/ml) of samples listed in table 1 in methanol/water 20:80 were used in the experiment. An LC/MS system as shown schematically in FIG. 3 was used with the following LC setup:
Thermo Fisher Scientific Vanquish® LC with autosampler and quaternary pump
10 μl injection (corresponds to 100 ng injected)
Thermo Fisher Scientific Accucore aQ column; 2.1×100 mm, 2.6 mm particle size
Solvent A: water, 0.1% FA, 2 mM ammonium acetate
Solvent B: methanol, 0.1% FA, 2 mM ammonium acetate
Gradient 100% A (0-0.5 min); 50% A/50% B (0.5-8.5 min); 20% A/80% B (8.5-9.0 min); 100% A (9.0-11.0 min) (step gradient)
Divert valve switching at t=2.75 min and t=8.00 min FIG. 11 shows the solvent step gradient used in the experiment. In this experiment a reduced flow setup was used. As shown in FIG. 3, a tee was inserted into the flow path before the LC column and connected to a HPLC switching valve. The valve could be switched to either of two positions: i) a blocked port, or ii) a port connected to a flow restriction capillary going to waste. If the valve was switched to position i), all flow went through the column. When switched to position ii), only a fraction of the flow went through the column, extending the time taken to elute a peak from the column. This lead to significant peak broadening. In this case, peak width was extended from 0.5 min to approx. 6 minutes. Due to the characteristics of the electrospray ionization method, the signal intensity was not significantly affected by the drop in the flow rate, effectively extending the analysis time and multiplying the number of measurement points by the ratio of the peak widths. It will be appreciated that the reduced flow rate could also be implemented using a set-up as shown in FIG. 2 by reducing the pump speed (pressure) for the required duration. The reduced flow rate approach gave a much better precision of the isotope ratio measurement.

Figure 12:
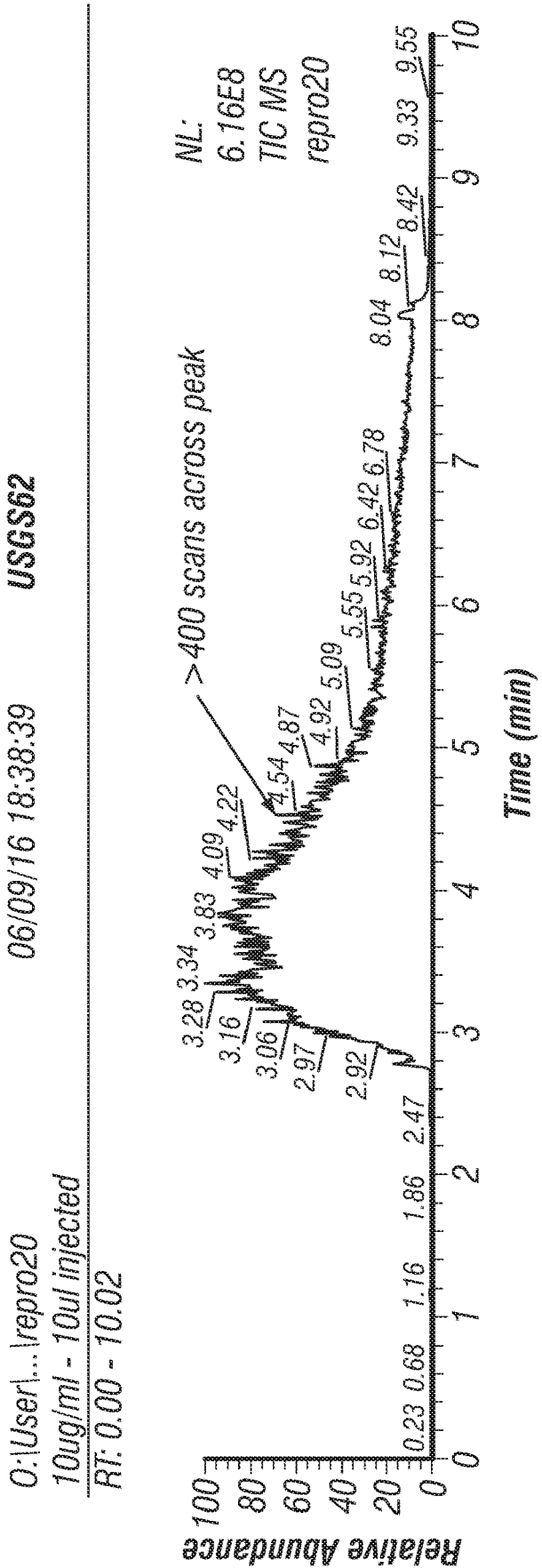
FIG. 12 shows a chromatogram, mass spectrum and LC pump pressure v. time profile obtained in an LC/MS experiment using reduced flow.
Figure 12:
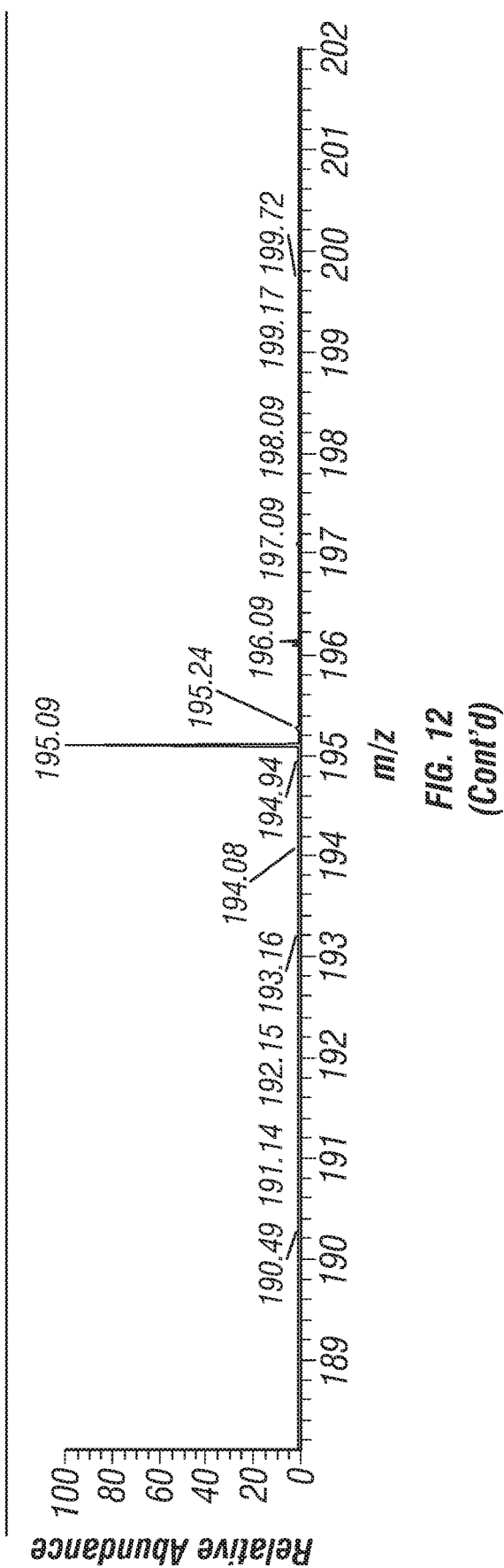
Figure 12:
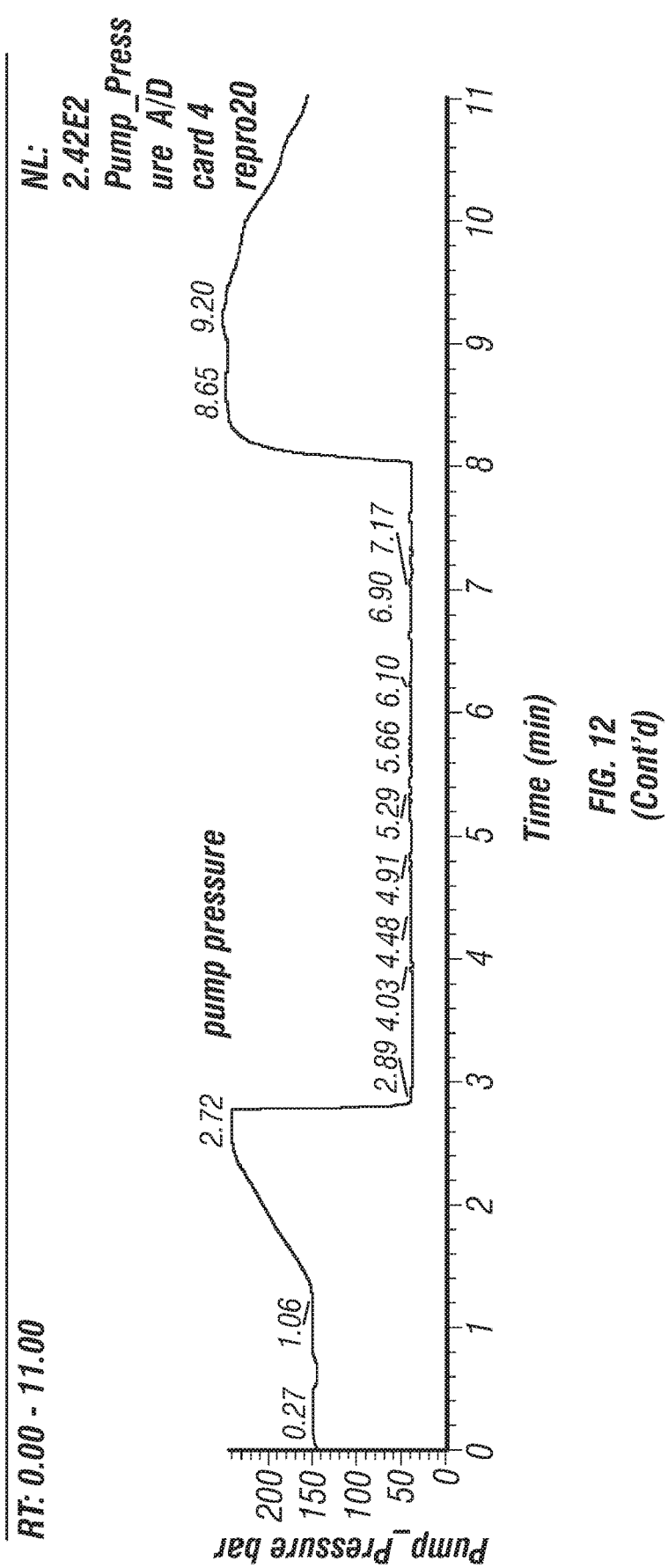
Figure 13:
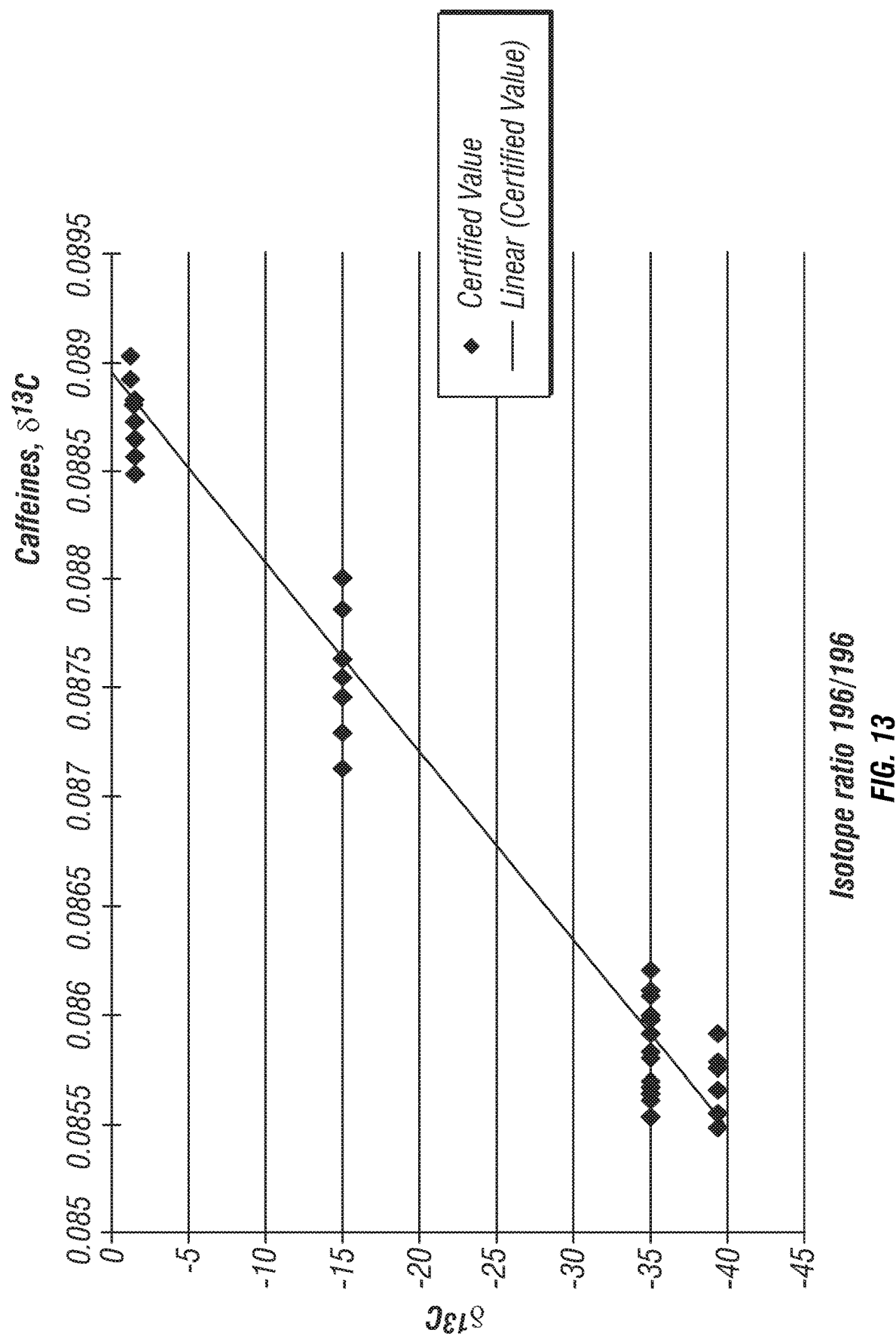
FIG. 13 shows a plot of measured isotope ratios of caffeine vs. known certified $\delta\ ^{13}C$ values from an LC/MS experiment using reduced flow.

The mass spectrometer was operated using the following parameters:
Mass scan/isolation range 190-200 m/z
Resolving power=240 k @ m/z 200
1 microscan per transient processed
Target AGC value 1E6
4 min total data acquisition The acquisition and data evaluation strategy employed the following:
Sample/standard bracketing
USGS1 as reference/standard
8 repetitions of bracketing set (49 injections total)
Data evaluation using USGS1 measurements to correct drift
Direct calculation of δ values; no additional corrections FIG. 12 shows a typical chromatogram, mass spectrum and LC pump pressure v. time profile. With the LC peak width of caffeine increased to approx. 6 min, this resulted in approx. 400 scans across the LC peak. Table 4 shows the results of the measurements and FIG. 13 shows the plot of the measured isotope ratios vs. the known certified $\delta$ $^{13}C$ values together with the linear calibration curve. The standard error of each single measurement was approximately 0.7-0.9‰ and the accuracy of the method was approx. 2‰. It can be seen that the reduced flow approach of the invention enables reliable determination of precise and accurate isotope ratios of molecular species using high resolution mass spectrometry (e.g. ORBITRAP mass spectrometry) coupled to liquid chromatography or another liquid separation.

TABLE 4

| Sample | $\delta^{13}C$ (‰) (measured) | StdErr (‰) | Stdev (‰) | $\delta^{13}C$ (‰) Certified Value |
|---|---|---|---|---|
| USGS61 | −35.05 | N/A | N/A | −35.05 |
| USGS62 | −14.45 | 0.79 | 2.25 | −14.97 |
| USGS63 | −1.36 | 0.77 | 2.18 | −1.17 |
| BRE001 | −37.86 | 0.64 | 1.81 | −39.21 |

Herein the term mass to charge ratio (m/z) in relation to the mass analysis means any quantity of the mass analysis related to m/z, for example mass, time (e.g. flight time in a TOF mass analysis), frequency (e.g. ion oscillation frequency in a Fourier transform mass analysis) etc.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc., mean "including but not limited to", and are not intended to (and do not) exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A method of isotope ratio mass spectrometry comprising:
    flowing a liquid mobile phase that contains a sample through a separation device at a first flow rate, the sample comprising at least one molecular species having an isotope ratio to be determined, wherein the first flow rate is at least 50% of an optimum flow rate corresponding to a minimum theoretical plate height of the separation device;
    reducing the flow rate of the liquid mobile phase flowing through the separation device from the first flow rate to a second flow rate that is lower than the first flow rate but corresponds to a higher theoretical plate height of the separation device for at least a portion of time that the at least one molecular species is emerging from the separation device, the second flow rate is selected to produce a desired isotope ratio precision;
    mass analyzing the at least one molecular species that has emerged from the separation device at least while the flow rate is reduced to the second flow rate; and
    determining from the mass analysis at least one isotope ratio of the at least one molecular species from the intensities of mass peaks of at least two isotopologues of the at least one molecular species, wherein the mass analysis is performed with mass resolving power high enough to resolve the two most abundant mass peaks at the nominal mass of at least one of the isotopologues.

2. The method of claim 1 wherein the separation device is a liquid chromatography column, size-exclusion chromatography (SEC) column, ion chromatography (IC) column, thin-layer chromatography (TLC) plate, or capillary electrophoresis (CE) system.

3. The method of claim 1 wherein the separation device is a liquid chromatography column, wherein the column has an internal diameter and wherein reducing the flow rate comprises reducing the flow rate from the first rate to the second flow rate having a value in mL/min that is less than half the value given by 0.06×(internal diameter in mm)$^2$.

4. The method of claim 1 wherein the liquid mobile phase comprises an organic solvent.

5. The method of claim 1 wherein the flow rate is reduced to the second flow rate for at least substantially the whole of the time that the at least one molecular species is eluting from the separation device.

6. The method of claim 1 wherein the isotope ratio is determined with an isotope ratio precision of <20 δ‰.

7. The method of claim 1 wherein the flow rate is increased from the second flow rate once the at least one molecular species has substantially finished eluting from the separation device.

8. The method of claim 1 wherein the second flow rate is reduced by a factor of at least 5 compared to the first flow rate.

9. The method of claim 1 wherein the first flow rate is at least 80% of the optimum flow rate and the second flow rate is less than 20% of the optimum flow rate, wherein the second flow rate is reduced relative to the first rate by a factor of at least 5.

10. The method of claim 1 wherein the flow rate is reduced from the first flow rate to the second flow rate by reducing a pump speed of a pump that is flowing the liquid mobile phase through the separation device.

11. The method of claim 1 wherein the flow rate is reduced from the first flow rate to the second flow rate by splitting the flow of mobile of phase upstream of the separation device so that a reduced flow rate of mobile phase passes through the separation device.

12. The method of claim 1 wherein the mass analysis is performed by a high resolution accurate mass (HR-AM) mass spectrometer.

13. The method of claim 1 wherein the mass analysis is performed with a mass resolving power high enough to resolve the two most abundant A+1 isotopologues and/or the two most abundant A+2 isotopologues of the at least one molecular species, where A is the monoisotopic mass peak.

14. The method of claim 1 wherein the mass analysis is performed with a resolving power of at least 50,000.

15. The method of claim 1 wherein the mass analysis is performed using a mass spectrometer comprising a mass analyzer selected from: an electrostatic orbital trap mass analyzer, an FT-ICR mass analyzer, or a time of flight TOF mass analyzer.

16. The method of claim 1 wherein the mass analysis comprises ionizing the at least one molecular species before ejecting the ions to a mass analyzer for mass analysis.

17. The method of claim 16 wherein the mass analysis comprises fragmenting the ionized at least one molecular species prior to mass analysis.

18. The method of claim 17 wherein determining at least one isotope ratio of the at least one molecular species comprises determining position specific information about the determined isotope ratio.

19. The method of claim 1 wherein determining at least one isotope ratio of the at least one molecular species comprises comparing the intensity of a monoisotopic mass peak A with an A+1 mass peak or A+2 mass peak to provide an isotope ratio of a light isotope and a heavy isotope of interest.

20. The method of claim 19 wherein the mass analysis resolves two or more A+1 isotopologues and/or two or more A+2 isotopologues.

21. The method of claim 19 wherein the light isotope is selected from $^{12}C$, $^{14}N$, $^{16}O$, $^{1}H$, $^{32}S$, $^{35}Cl$, $^{79}Br$, $^{28}Si$ and the heavy isotope is selected from $^{13}C$, $^{14}C$, $^{15}N$, $^{17}O$, $^{18}O$, $^{2}H$, $^{34}S$, $^{37}Cl$, $^{81}Br$, $^{29}Si$, $^{30}Si$.

22. The method of claim 1 wherein determining at least one isotope ratio of the at least one molecular species comprises comparing the intensity of two peaks having the same nominal mass, being either two A+1 mass peaks or two A+2 mass peaks.

23. The method of claim 1, further comprising calibrating the at least one isotope ratio determined from the intensities of mass peaks of at least two isotopologues against one or more isotope ratios for one or more known standards.

24. A method of isotope ratio mass spectrometry comprising:
flowing a liquid mobile phase that contains a sample through a separation device at a first flow rate, the sample comprising at least one molecular species having an isotope ratio to be determined, wherein the first flow rate is at least 50% of an optimum flow rate corresponding to a minimum theoretical plate height of the separation device;
reducing the flow rate of the liquid mobile phase flowing through the separation device from the first flow rate to a second flow rate that is lower than the first flow rate but corresponds to a higher theoretical plate height of the separation device for at least a portion of time that the at least one molecular species is emerging from the separation device, the second flow rate is selected to produce a desired isotope ratio precision;
mass analyzing the at least one molecular species that has emerged from the separation device at least while the flow rate is reduced to the second flow rate; and
determining from the mass analysis at least one isotope ratio of the at least one molecular species from the intensities of mass peaks of at least two isotopologues of the at least one molecular species, wherein each isotopologue mass peak used for the isotope ratio determination is resolved from at least any other mass peaks at the same nominal mass which are more than 20% of the intensity of the isotopologue mass peak.

25. An apparatus for isotope ratio mass spectrometry comprising:
a separation device for separating components of a sample in a liquid mobile phase, the components of the sample comprising at least one molecular species having an isotope ratio to be determined;
a mass spectrometer coupled to the separation device downstream for mass analyzing the at least one molecular species as the at least one molecular species elutes from the separation device and determining from the mass analysis at least one isotope ratio of the at least one molecular species, wherein the mass analysis is performed with mass resolving power high enough to resolve the two most abundant mass peaks at the nominal mass of at least one of the isotopologues; and
a controller configured to control the flow of the liquid mobile phase through the separation device, to flow the liquid mobile phase through the separation device for a first portion of time at a first flow rate and to reduce the flow rate of the liquid mobile phase through the separation device from the first flow rate to a second flow rate lower than the first flow rate for at least a portion of time that the at least one molecular species is eluting from the separation device, the second flow rate is selected to produce a desired isotope ratio precision.

* * * * *